US006290911B1

(12) United States Patent
Lewis et al.

(10) Patent No.: US 6,290,911 B1
(45) Date of Patent: Sep. 18, 2001

(54) COMPOSITIONALLY DIFFERENT POLYMER-BASED SENSOR ELEMENTS AND METHOD FOR PREPARING SAME

(75) Inventors: Nathan S. Lewis, La Canada; Robert H. Grubbs, Pasadena; Robert D. Sanner, Livermore; Eric J. Severin, San Marino, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/106,791

(22) Filed: Jun. 29, 1998

Related U.S. Application Data
(60) Provisional application No. 60/051,203, filed on Jun. 30, 1997.

(51) Int. Cl.[7] .................................................. G01N 27/02
(52) U.S. Cl. ................. 422/82.02; 422/68.1; 422/82.01; 422/83; 422/98; 204/406; 204/412; 204/431
(58) Field of Search ........................ 422/68.1, 69, 82.01, 422/82.02, 83, 84, 90, 98; 204/406, 412, 422, 424; 436/149

(56) References Cited

U.S. PATENT DOCUMENTS

| | | | |
|---|---|---|---|
| 3,045,198 | 7/1962 | Dolan et al. | 338/13 |
| 4,542,640 | 9/1985 | Clifford | 73/23 |
| 4,631,952 | 12/1986 | Donaghey | 73/23 |
| 4,759,210 | 7/1988 | Wohltjen | 73/23 |
| 4,855,706 | 8/1989 | Hauppty | 338/34 |
| 4,871,680 | 10/1989 | Barraud et al. | 436/103 |
| 4,907,441 | 3/1990 | Shurmer | 73/23 |
| 4,992,244 | 2/1991 | Grate | 422/98 |
| 5,045,285 | 9/1991 | Kolesar, Jr. | 422/98 |
| 5,120,421 | 6/1992 | Glass et al. | 204/406 |
| 5,256,574 | 10/1993 | Neuberger et al. | 436/143 |
| 5,334,351 | 8/1994 | Heinze et al. | 422/90 |
| 5,417,100 | 5/1995 | Miller et al. | 73/31 |
| 5,512,882 | 4/1996 | Stetter et al. | 340/632 |
| 5,571,401 * | 11/1996 | Lewis et al. | 205/787 |
| 5,623,212 | 4/1997 | Yamanaka | 324/693 |
| 5,654,497 | 8/1997 | Hoffheins et al. | 73/23.2 |
| 5,675,070 | 10/1997 | Gelperin | 73/23.34 |
| 5,788,883 * | 8/1998 | Lewis et al. | 205/787 |

FOREIGN PATENT DOCUMENTS

| | | |
|---|---|---|
| 0 596 973 B1 | 5/1994 | (EP) . |
| 0 794 428 A1 | 9/1997 | (EP) . |
| WO 96/07901 A1 | 3/1996 | (WO) . |

OTHER PUBLICATIONS

Andrieux, Claude, et al., "Observation of the Cation Redicals of Pyrrole and of Some Substituted Pyrroles in Fast–Scan Cyclic Voltammetry," Standard Potentials and Lifetimes, J. Am. Chem. Soc., 112, pp. 2439–2440 (1990).

Barlett, P.N., et al., "Electrochemical Deposition of Conducting Polymers onto Electronic Substrates for Sensor Applications," Sensors and Actuators A, A21–A23, pp. 911–914 (1990).

Bidan, G. et al., "Polypyrrole and poly(N–methylpyrrole) films doped with Keggin–type heteropolyanions: preparation and properties," J. Electroanal. Chem., 251, pp. 297–306 (1988).

Charlesworth, John, et al., "Mechanistic Studies on the Interactions between Poly(pyrrole)and Organice Vapors," J. Phys. Chem., 97, pp. 5418–5423 (1992).

Corcoran, P., et al., "Integrated tin oxide sensors of low power consumption for use in gas and odour sensing," Sensors and Actuators B, 15–16, pp. 32–37 (1993).

DeVries, Steven, et al., "Synaptic Circuitry of the Retina and Olfactory Bulb," Cell/Neuron, 72/10 (Suppl) pp. 139–149 (1993).

Diaz, A.F., et al., "Electrooxidation of Aromatic Oligomers and Conducting Polymers," J. Electr. Chem., 121, pp. 355–361 (1981).

Dickinson, Todd A., et al., "A chemical–detecting system based on a cross–reactive optical sensor array," Nature, vol. 382, No. 22, pp. 697–699, Aug. 22, 1996.

Dickinson, Todd A., et al., "Generating Sensor Diversity through Combinatorial Polymer Synthesis," Analytical Chemistry, vol. 69, No. 17, pp. 3413–3418, Sep. 1, 1997.

Gardner, Julian W., et al., "Integrated Tin Oxide Odour Sensors," Sensors and Actuators B, 4, pp. 117–121 (1991).

Gardner, Julian W., et al., "Application of an electronic nose to the discrimination of coffees," Sensors and Actuators B, 6, pp. 71–75 (1992).

Gardner, Julian W., et al., "Design of Conducting Polymer Gas Sensors: Modelling and Experiment," Synthetic Metals, vol. 55–57, pp. 3665–3670 (1993).

Gardner, Julian W., et al., "Detection of vapours and odours from a multisensor array using pattern–recognition. Par 2. Artificial Neural Networks,"Sensors and Actuators B, 9, pp. 9–15 (1992).

(List continued on next page.)

*Primary Examiner*—Jeffrey Snay
*Assistant Examiner*—Dwayne K. Handy
(74) *Attorney, Agent, or Firm*—Townsend & Townsend & Crew LLP

(57) ABSTRACT

The present invention provides a combinatorial approach for preparing arrays of chemically sensitive polymer-based sensors which are capable of detecting the presence of a chemical analyte in a fluid in contact therewith. The described methods and devices comprise combining varying ratios of at least first and second organic materials which, when combined, form a polymer or polymer blend that is capable of absorbing a chemical analyte, thereby providing a detectable response. The detectable response of the sensors prepared by this method is not linearly related to the mole fraction of at least one of the polymer-based components of the sensors, thereby making arrays of these sensors useful for a variety of sensing tasks.

24 Claims, 9 Drawing Sheets

OTHER PUBLICATIONS

Gardner, Julian W., et al., "Detection vappours and odours from a multisensor array using pattern–recognition Part 1. Principal Component and Cluster Analysis," Sensors and Actuators B, 4, pp. 109–115 (1991).

Gardner, Julian W., et al., "A multisensor system for beer flavor monitoring using an array of conducting polymer and predictive classifiers," Sensors and Actuators B, 18–19, pp. 240–243 (1994).

Gardner, Julian W., et al., "A brief history of electronic noses," Sensors and Actuators B, 18–19, pp. 221–220 (1994).

Grate, Jay W., et al., "Solubility interactions and the design of chemically selective sorbent coatings for chemical sensors and arrays," Sensors and Actuators B, 3, pp. 85–111 (1991).

Grate, Jay W., et al., "Smart Sensor System for Trace Organophosphorous and Organosulfur Vapor Detection Employing a Temperature–Controlled Array of Surface Acoustic Wave Sensors, Automated Sample Preconcentration and Pattern Recognition," Anal. Chem., 65, pp. 1868–1881 (1993).

Hecht, *Mathematics in Chemistry: An Introduction to Modern Methods*, Prentice Hall, Enflewood Cliffs, NJ, Ch. 5, pp. 256–335 (1990).

Johnson, Stephen R., et al., "Identification of Multiple Analytes Using an Optical Sensor Array and Pattern Recognition Neural Networks," Analytical Chemistry, vol. 69, No. 22, pp. 4641–4648, Nov. 15, 1997.

Kanzawa, K.K., et al., "Electrical Properties of Pyrrole and its Copolymers," Synthetic Metals, 4, 119–130 (1981).

Kauer, John S., "Contributions of topography and parallel processing to odor coding in the vertebrate olfactory pathway," TINS, vol. 14, No. 2, pp. 79–85 (1991).

Kaufman, J.H., et al., "Evolution of Polaron States into Bipolarons in Polypyrrole," Physical Review Letters, vol. 53, No. 19, pp. 1005–1008 (1994).

Lancet, Doron, et al., "Olfactory receptors," Current Biology, vol. 3, No. 10, pp. 668–674 (1993).

Lewis, Nathan, "The Caltech Electronic Nose Project," Engineering & Science, No. 3, pp. 3–13, 1996.

Lonergan, Mark C., et al., "Array–Based Vapor Sensing Using Chemically Sensitive, Carbon Black–Polymer Resistors," Division of Chemistry and Chemical Engineering, California Institute of Technology, XP–002078727, Chemical Material, No. 8, pp. 2298–2312, 1996.

Lonergan, Mark C., et al., "Array–Based Vapor Sensing Using Chemically Sensitive, Polymer Composite Resistors," Division of Chemistry and Chemical Engineering, California Institute of Technology, XP–002078726, pp. 583–631.

Lundstrom, I., et al., "Artificial 'Olfactory' images from a chemical sensor using a light–pulse techique," Nature, vol. 352, pp. 47–50 (1991).

Morris, A.C., et al., "The System Ethanol–Methanol at 40° C., " Canadian Journal of Research, vol. 20, Sec. B, pp. 207–211 (1942).

Pearce, Timothy C., et al., "Electronic Nose for Monitoring the Flavour of Beers," Analyst, vol. 118, pp. 371–377 (1993).

Pope, *Heteropoly and Isopoly Oxometalates* (Springer–Verlag, New York), Ch. 4, pp. 58–90 (1983).

Reed, Randall R., "Signaling Pathways in Ordorant Detection," Neuron, vol. 8, pp. 205–209 (1992).

Salmon, M., et al., "A Chemical Route to Pyrrole Polymer Films," Journal of Polymer Science, 20–3, pp. 187–193 (1982).

Shurmer, Harold V., et al., "Odour Discrimination with an electronic nose," Sensors and Actuators B, 8, pp. 1–11 (1992).

Shurmer, Harold V., et al., "Integrated Arrays of Gas Sensors Using Conducting Polymers with Molecular Sieves," Sensors and Actuators B, 4, pp. 29–33 (1991).

Stetter, J.R., et al., "Detection of Hazardous Gases and Vapors: Pattern Recognition Analysis of Data from an Electrochemical Sensor Array," Anal. Chem., 58, pp. 860–866 (1986).

Stetter, J.R., et al., "Quality classification of grain using a sensor array and pattern recognition," Analytica Chimica Acta, 284, pp. 1–11 (1993).

Stetter, J.R., et al., "Sensor Array and Catalytic Filament for Chemical Analysis of Vapors and Mixtures," Sensors and Actuators, B1 pp. 43–47 (1990).

Topart, Patrice, et al., "Characterization of the Interaction between Poly(pyrrole) Films and Methanol Vapor," J. Phys. Chem., 96, pp. 7824–7830 (1992).

White, Joel, et al., "Rapid Analyte Recognition in a Device Based on Optical Sensors and the Olfactory System," Analytical Chemistry, vol. 68, No. 13, pp. 2191–2202, Jul. 1, 1996.

Yakushi, K., et al., "Optical study of Polypyrrole perchlorate," J. Chem. Physics, 79(10), pp. 4774–4778 (1983).

Zaromb, S., et al., "Theoretical Basis for Identification and Measurement of Air Contaminants using an array of sensors having partly overlapping selectivities," Sensors and Actuators, 6, pp. 225–243 (1984).

\* cited by examiner

FIGURE 3

| At concentration x: | | | | | |
|---|---|---|---|---|---|
| | $P_1$ | $P_2$ | $P_3$ | $P_4$ | ...$P_n$ |
| $P_1$ | $P_1$ | $P_{2[x]}P_{1[y]}$ | $P_{3[x]}P_{1[y]}$ | $P_{4[x]}P_{1[y]}$ | $P_{n[x]}P_{1[y]}$ |
| $P_2$ | $P_{1[x]}P_{2[y]}$ | $P_2$ | $P_{3[x]}P_{2[y]}$ | $P_{4[x]}P_{2[y]}$ | $P_{n[x]}P_{2[y]}$ |
| $P_3$ | $P_{1[x]}P_{3[y]}$ | $P_{2[x]}P_{3[y]}$ | $P_3$ | $P_{4[x]}P_{3[y]}$ | $P_{n[x]}P_{3[y]}$ |
| $P_4$ | $P_{1[x]}P_{4[y]}$ | $P_{2[x]}P_{4[y]}$ | $P_{3[x]}P_{4[y]}$ | $P_4$ | $P_{n[x]}P_{4[y]}$ |
| ...$P_n$ | $P_{1[x]}P_{n[y]}$ | $P_{2[x]}P_{n[y]}$ | $P_{3[x]}P_{n[y]}$ | $P_{4[x]}P_{n[y]}$ | $P_n$ |

At concentration y:

FIGURE 4

| At concentration x: | | | | | |
|---|---|---|---|---|---|
| | $P_1$ | $P_2$ | $P_3$ | $P_4$ | ...$P_n$ |
| $P_{n+1}$ | $P_{1[x]}P_{n+1[y]}$ | $P_{2[x]}P_{n+1[y]}$ | $P_{3[x]}P_{n+1[y]}$ | $P_{4[x]}P_{n+1[y]}$ | $P_{n[x]}P_{n+1[y]}$ |
| $P_{n+2}$ | $P_{1[x]}P_{n+2[y]}$ | $P_{2[x]}P_{n+2[y]}$ | $P_{3[x]}P_{n+2[y]}$ | $P_{4[x]}P_{n+2[y]}$ | $P_{n[x]}P_{n+2[y]}$ |
| $P_{n+3}$ | $P_{1[x]}P_{n+3[y]}$ | $P_{2[x]}P_{n+3[y]}$ | $P_{3[x]}P_{n+3[y]}$ | $P_{4[x]}P_{n+3[y]}$ | $P_{n[x]}P_{n+3[y]}$ |
| $P_{n+4}$ | $P_{1[x]}P_{n+4[y]}$ | $P_{2[x]}P_{n+4[y]}$ | $P_{3[x]}P_{n+4[y]}$ | $P_{4[x]}P_{n+4[y]}$ | $P_{n[x]}P_{n+4[y]}$ |
| ...$P_{n+m}$ | $P_{1[x]}P_{n+m[y]}$ | $P_{2[x]}P_{n+m[y]}$ | $P_{3[x]}P_{n+m[y]}$ | $P_{4[x]}P_{n+m[y]}$ | $P_{n[x]}P_{n+m[y]}$ |

At concentration y:

COMPOSITIONALLY DIFFERENT POLYMER-BASED SENSOR ELEMENTS AND METHOD FOR PREPARING SAME

This is based on a provisional application, U.S. Ser. No. 60/051,203, filed on Jun. 30, 1997, the contents of which are expressly incorporated herein by reference.

FIELD OF THE INVENTION

The present invention is directed to novel devices and methods for preparing and using a plurality of compositionally different sensors that are capable of detecting the presence of a chemical analyte in a fluid.

There is considerable interest in developing chemically sensitive sensors that are capable of detecting the presence of a particular chemical analyte in a fluid for the purpose of achieving a detectable response. Such sensors are often fabricated from a polymeric organic material that is capable of absorbing a chemical analyte which comes in contact therewith, wherein absorbance of the analyte causes the polymeric material to swell, thereby providing a response that is capable of being detected. Variability in the ability to absorb an analyte results in variability in the detectable signal produced. Such organic polymer-based sensors have found use in a variety of different applications and devices including, for example, devices that function as analogs of the mammalian olfactory system (Lewis, U.S. Pat. No. 5,571,401 (incorporated herein by reference), Lundstrom et al., Nature 352:47–50 (1991) and Shurmer and Gardner, Sens. Actuators B 8:1–11 (1992)), bulk conducting polymer films (Barker et al., Sens. Actuators B 17:143 (1994) and Gardner et al., Sens. Actuators B 18:240 (1994)), surface acoustic wave devices (Grate et al., Anal. Chem. 67:2162 (1995), Grate et al., Anal. Chem. 65:A987 (1993) and Grate et al., Anal. Chem. 65:A940 (1993)), fiber optic micromirrors (Hughes et al., J. Biochem. and Biotechnol. 41:77 (1993)), quartz crystal microbalances (Chang et al., Anal. Chim. Acta 249:323 (1991)) and dye impregnated polymeric coatings on optical fibers (White et al., Anal. Chem. 68:2191 (1996)). These and all other references cited herein are expressly incorporated by reference as if set forth herein in their entirety. To date, however, many of the sensors employed in the above-described devices have been fabricated from limited numbers of polymeric components and, therefore, are limited in the responses that they are capable of producing.

Further, today's technology lags far behind the ability of canines or humans to detect or distinguish between chemical analytes. As a consequence, certain work is limited by the suitability of animals or humans to execute tasks. For example, quality control of food products can require production line employees to smell each item. Unfortunately, the ability of individuals to adequately discriminate odors diminishes after a short period of time, e.g., in about two hours. In addition, mammalian olfactory senses are limited in their ability to identify certain vapors. For example, water vapor is not detectable by smell. Further, mammalian olfactory senses are limited to identifying gaseous components, with no ability to identify or "smell" solutes in liquids.

There have been several attempts to construct sensors that can mimic or exceed the capability of olfactory organs. Such attempts have employed, for example, heated metal oxide thin film resistors, polymer sorption layers on the surfaces of acoustic wave resonators, fiber optic micromirrors, arrays of electrochemical detectors, and conductive polymers. Each of these techniques, however, has significant limitations in reproducibility, the ability to discriminate between analytes, or the time required for response. Further, these techniques are often prohibitively expensive or complicated.

Arrays of metal oxide thin film resistors, for example, are typically based on $SnO_2$ films that have been coated with various catalysts. Furthermore, these arrays generally do not allow deliberate chemical control of the response of elements in the array and the reproducibility of response from array to array is often poor. For example, the use of surface acoustic wave resonators, employs a signal transduction mechanism that involves complicated electronics and a frequency measurement to one Hz while sustaining a 200 MHz Rayleigh wave in the crystal. Therefore, a need exists for devices and methods to identify and measure analytes in fluids that overcome or minimize these problems.

Recent studies have shown that arrays of chemically sensitive sensors, formed from a library of swellable insulating organic polymers containing electrically conducting carbon black, are broadly responsive to a variety of analytes, yet allow classification and identification of organic vapors through application of pattern recognition methods. (Lonergan et al., Chem. Mater. 8:2298 (1996)). To date, these array elements have been fabricated from a relatively small number of approximately 10–20 organic polymers, with a single distinct polymer backbone composition in each sensor element. Although a limited number of polymeric sensor compositions might be chosen to perform optimally for specific applications, attempts to perform complex applications, such as to mimic the sense of olfaction, in which the sensing task is time dependent or is not defined in advance of the sensor array construction, will almost certainly require use of polymeric sensor libraries that are far more extensive and compositionally diverse than those presently known. Thus, there is a need for novel methods for producing large libraries of compositionally distinct chemically sensitive sensors, each of which are capable of producing a detectable response in the presence of a chemical analyte of interest.

SUMMARY OF THE INVENTION

While methods for producing a plurality of compositionally distinct chemically sensitive sensors may prove to be very useful in a variety of applications, the utility of such methods is dependent upon whether the response produced by each of the compositionally distinct sensors is a linear function of the mole fraction of any particular component of the sensor. In other words, if the response provided by a sensor is a direct linear function of the mole fraction of a particular component of the sensor, then not much additional information will be obtained from the responses of sensors that comprise a mixture of two different polymeric materials over those sensors that are fabricated solely from one or the other polymeric material. Thus, nonlinearity in the response profile as compared to the mole fraction of an organic material present in the plurality of the sensors is very important for increasing the power of these sensor arrays to resolve multitudes of analytes.

Therefore, it is an object of the present invention to provide a combinatorial approach to the construction of sensor arrays in which blends of two or more organic materials are used as a feedstock to create compositionally varying chemically sensitive sensor films.

It is also an object of the present invention to provide (i) novel methods for making and using a plurality of compositionally different sensors, each of which comprise at least two different organic materials and that are capable of detecting the presence of a chemical analyte in a fluid, and (ii) novel devices made by these methods.

It is another object of the present invention to provide (i) novel methods for making and using a plurality of compositionally different sensors, each of which provide a detectable signal in response to the presence of a chemical analyte, and wherein the detectable signal is not linearly related to the mole fraction of any organic material present in the sensor; and (ii) novel devices made by these methods.

It is yet another object of the present invention to provide (i) novel methods for making and using a plurality of chemically sensitive sensors that can be employed in any system that is dependent upon analyte uptake to achieve a detectable response, and (ii) novel devices made by these methods. Such systems include, for example, analogs to the mammalian olfactory system, arrays of coated surface acoustic wave sensors, fiber optic micromirrors, quartz crystal microbalance sensors, polymer-coated fiber optic sensors, and the like.

It is another object of the present invention to provide (i) novel methods for making a plurality of chemically sensitive sensors, wherein those methods are quick, easy, inexpensive and are capable of providing large numbers of compositionally distinct sensors for use in vapor detection; and (ii) novel devices made by these methods.

These and further objects will be apparent to the ordinarily skilled artisan upon consideration of the specification as a whole.

In accordance with the present invention, novel methods are provided for preparing a plurality of compositionally different sensors that are capable of detecting the presence of a chemical analyte in a fluid, and, thereby, provide a detectable response. As used herein, the term "fluid" includes both gases and liquids. Specifically, an embodiment of the present invention is directed to methods for making a plurality of compositionally different sensors that are capable of detecting the presence of an analyte in a fluid. The methods comprise combining different ratios of at least first and second organic materials. The first and second organic materials will generally be different and form an organic polymer or polymer blend when combined, and the step of combining provides a plurality of compositionally different sensors that comprise a variable mixture of the first and second organic materials. Each of the sensors provides a detectable signal in response to the presence of the chemical analyte, which signal is not linearly related to the mole fraction of at least one of the organic materials, and more preferably both of the organic materials present in the sensors. The devices made by these methods are also disclosed.

In accordance with the present invention, the first and second organic materials may be combined simultaneously to produce the array of sensors, or the organic components may be combined at different times to produce the plurality of sensors, neither being critical to the invention. In one embodiment, the first and second organic materials are each organic polymers, thereby providing a plurality of sensors each of which comprise an organic polymer blend. In another embodiment, the first and second organic materials may be organic monomer units which, when combined, polymerize, either with or without the presence of a catalyst, to form an organic polymer.

In still another embodiment, the first organic material is a homopolymer or copolymer, and the second organic material is a monomer which is combined with the first material. When the monomer is polymerized in the presence of the first, preformed polymer, the monomer polymerizes to produce an interpenetrating network (IPN) of first and second organic materials. This technique is particularly suitable for achieving blends when dealing with polymers that are imicible in one another, and/or where the polymers are made from monomers that are volatile. Under these conditions, the preformed polymer is used to dictate the properties (e.g., viscosity) of the polymer-monomer mixture. Thus, the polymer holds the monomer in solution. Examples of such systems are (1) preformed polyvinyl acetate with monomer methylmethacrylate to form an IPN of pVA and pMMA, (2) preformed pVA with monomer styrene to form an IPN of pVA and polystyrene, and (3) preformed pVA with acrylonitrile to form an IPN of pVA and polyacrylonitrile. More than one monomer may be used where it is desired to create an IPN having one or more copolymers.

In yet another embodiment of the present invention, an electrically conductive material, which may be a single electrically conductive material or a mixture of two or more electrically conductive materials, is added to a polymer, polymer blend, or stabilized colloid. In a preferred embodiment of the present invention, the electrically conductive material is a conductive polymer or carbon black. When an electrically conductive material is added to the sensors, the sensors provide (i) an electrical path for an electrical current, (ii) a first electrical resistance in the electrical path in the absence of the chemical analyte and (iii) a second resistance in the electrical path in the presence of the chemical analyte. The first and second electrical resistances may be either the same or different, depending upon the analyte being analyzed and the ability of that sensor to sorb (either absorb or adsorb) that analyte.

One embodiment is an electronic nose that mimics a mammalian olfactory system. This embodiment includes a substrate having a plurality of sensors, where each sensor includes a chemically sensitive resistor that includes a combination of a first nonconductive organic material at a concentration, a second nonconductive organic material at a concentration and a conductive material. The first nonconductive organic material is different from the second nonconductive organic material and the number of array sensors is greater than the number of different nonconductive organic materials which form the array sensors. The electronic nose also includes an electrical measuring apparatus electrically connected to the array sensors.

Another embodiment of the electronic nose includes at least two chemically sensitive resistors and an electrical measuring apparatus electrically connected to the resistors. Each chemically sensitive resistor includes a combination of a first nonconductive organic material at a concentration, a second nonconductive organic material at a concentration, and a conductive material, with the proviso that the first nonconductive organic material is different from the second nonconductive organic material. In one embodiment, the concentration of the first nonconductive organic material of the first resistor is different from the concentration of the first nonconductive organic material of the second resistor. In another embodiment, the first nonconductive organic material of the second resistor is the same as the first nonconductive organic material of the first resistor, and the concentration of the first nonconductive organic material of the first resistor is the same as the concentration of the first nonconductive organic material of the second resistor.

Methods of using the sensors are also provided. One embodiment is a method for detecting the presence of an analyte in a fluid, which includes the step of providing a plurality of sensors that includes at least two chemically sensitive resistors, each having a resistance response to the presence of the fluid and a resistance response to presence of the analyte, and an electrical measuring apparatus electrically connected to the resistors. Each chemically sensitive resistor includes a combination of a first nonconductive organic material at a concentration, a second nonconductive organic material, and a conductive material, with the proviso that the first nonconductive organic material in each resistor is different from the second nonconductive organic material in each resistor and with a further proviso that the concentration of the first nonconductive organic material in the first resistor is different from the concentration of the first nonconductive organic material in the second resistor. The resistors are then exposed to the fluid, and resistance responses are measured. Then, the measured resistance response of the first resistor is compared to the first measured resistance response of the second resistor to determine the presence of the analyte in the fluid.

In other embodiments, the sensors are combined with a wide variety of supporting technology to measure sensor response other than resistance. These embodiments include techniques that detect variations in electromagnetic energy, optical properties, capacitance, inductance or impedance and other physical, chemical and electrical properties that may vary in accordance with the response of the sensors. Thus, the number of applications sensing the presence of the analytes are very broad and also, therefore, the applications to which the sensors may be put is very broad.

Methods of manufacturing are also provided. One embodiment is a method of manufacturing an array of chemically sensitive sensors from a limited number of feedstock solutions of nonconductive organic materials in which the first step includes providing a first feedstock solution of a first organic material at a concentration x in a first solvent, a second feedstock solution of a second organic material in a second solvent at three different concentrations, y, y+b and y+c, and a substrate having first, second and third preselected regions. Next, each of the first, second and third regions is contacted with the first feedstock solution at concentration x. Then, the first region is contacted with the second feedstock solution at concentration y, the second region is contacted with the second feedstock solution at said concentration y+b, and the third region is contacted with the second feedstock solution at said concentration y+c. In this embodiment, the first organic material is different from the second organic material and y, y+b and y+c are each different concentrations. The resulting sensor array has a total number of sensors, one manufactured at each preselected region, that is greater than the number of feedstock solutions used to manufacture the sensors.

Other embodiments of the present invention are arrays of compositionally different sensors and methods of producing them. In certain embodiments, these arrays of sensors may be incorporated into devices that are capable of detecting the presence of an analyte in a fluid and/or may be placed in communication with apparati that are capable of measuring the signal produced by the array in response to the presence of a chemical analyte in a fluid. In some embodiments, the above-described plurality of sensors is incorporated into a device designed to detect the presence of an analyte in a fluid. Such devices include, for example, surface acoustic wave sensors, fiber optic micromirrors, quartz crystal microbalance sensors and polymer-coated fiber optic sensors.

Other embodiments of the present invention will become apparent to those of ordinary skill in the art upon a consideration of the specification as a whole.

BRIEF DESCRIPTION OF THE DRAWINGS

FIG. 3 shows a limited number (n) of polymer feedstock solutions at two different concentrations that have been combined to produce a greater number of combinatorial sensors.

FIG. 4 shows the effect of increasing the variety polymer feedstock solutions on the total number of sensors produced.

DETAILED DESCRIPTION OF THE INVENTION

Figure 1:
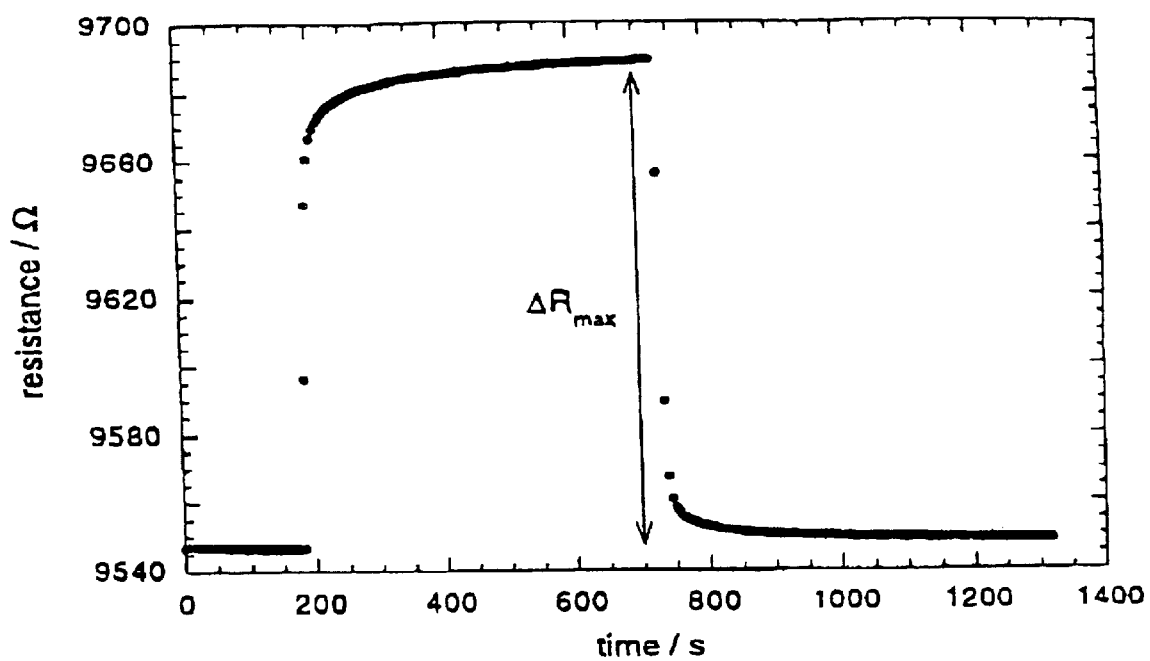
FIG. 1 shows the temporal response of a typical polymer composite chemiresistor sensor. This particular carbon black-containing composite sensor contained 55.1% poly (vinyl acetate) (PVA) and 44.9% poly(methyl methacrylate) (PMMA). The sensor was exposed to 13.9 parts per thousand (ppth) methanol in air for 540 seconds starting at the time point designated 180 seconds in the graph.

Novel methods are provided for manufacturing large numbers of chemically sensitive sensors starting from only a few base components. Specific embodiments are directed to methods of making and using a plurality of compositionally different polymer-based sensors that are capable of detecting the presence of an analyte in a fluid. Other embodiments are directed to the devices made by these methods. In one embodiment, the sensors prepared using the presently described method comprise a polymer or polymer blend material that is capable of sorbing a chemical analyte when, brought in contact therewith. In certain embodiments, the act of sorbing the chemical analyte causes the polymer or polymer blend to swell, thereby providing a response that is capable of being detected. Such swelling causes a volumetric change in the sensor. In embodiments where the sensor is a chemically sensitive resistor, such swelling causes a resistance response to permeation by the analyte. In certain embodiments, the resistance response is inversely proportional to the volumetric change. Because different polymers and polymer blends exhibit varying abilities to absorb different chemical analytes, arrays of compositionally distinct sensors will provide different responses to different analytes, those responses being capable of being detected and measured with an appropriate detection apparatus.

In order to prepare a plurality of compositionally different sensors as described herein, different ratios of at least first and second organic materials must be combined to form an organic polymer or an organic polymer blend. Organic materials that find use herein include organic polymers, and particularly nonconductive organic polymers, which are capable of absorbing a chemical analyte when brought into contact therewith as well as organic monomeric units which, when combined, polymerize to form an organic polymer. In the case where two or more organic polymers are combined to form a plurality of sensors, each sensor in the plurality will comprise a polymer blend (i.e., a blend of two or more different organic polymers). The two or more polymers added to form the polymer blend may be combined either simultaneously or one or more of the components may be added to the blend at different times. Preferably, only two different organic polymers are combined in varying ratios to form the plurality of sensors; however, three or more different polymers may also be employed.

In certain embodiments where the organic materials combined to form the sensors are monomers, those monomers, when combined or when significantly heated, exposed to light, etc., polymerize to form a single organic polymer. Again, as with the organic polymers discussed above, the monomer units may be added to create the sensors simultaneously or at different times. In other embodiments, the organic materials can be components of the same copolymer (a polymer made from two or more different monomers). In certain embodiments, the organic material can be oligomers. Certain embodiments of oligomers can have molecular weights between 400 and about 2,000. In still other embodiments, the organic material is a homopolymer (a polymer made from one monomer).

In still another embodiment, the first organic material is a homopolymer or copolymer, and the second organic material is a monomer which is combined with the first material. When the monomer is polymerized in the presence of the first, preformed polymer, the monomer polymerizes to produce an interpenetrating network (IPN) of first and second organic materials. This technique is particularly suitable for achieving blends when dealing with polymers that are imicible in one another, and/or where the polymers are made from monomers that are volatile. Under these conditions, the preformed polymer is used to dictate the properties (e.g., viscosity) of the polymer-monomer mixture. Thus, the polymer holds the monomer in solution. Examples of such systems are (1) preformed polyvinyl acetate with monomer methylmethacrylate to form an IPN of pVA and PMMA, (2) preformed pVA with monomer styrene to form an IPN of pVA and polystyrene, and (3) preformed pVA with acrylonitrile to form an IPN⁻ of pVA and polyacrylonitrile. More than one monomer may be used where it is desired to create an IPN having one or more copolymers.

Thus, the term "organic materials" is intended to encompass both organic polymers, and particularly nonconductive organic polymers, and monomers, which are capable of polymerizing to form an organic polymer.

A variety of different organic polymers may be employed as organic materials in the chemically sensitive sensors described herein. Certain of these polymers are discussed in Lewis et al., U.S. Pat. No. 5,571,401, incorporated herein by reference in it entirety for all purposes. In certain embodiments, the organic materials include main-chain carbon polymers such as poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), and the like, main-chain acrylic heteroatom organic polymers such as poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), and the like, and main-chain heterocyclic polymers such as poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, and the like. In a preferred embodiment, the polymers employed are poly(vinyl acetate) (PVA) and poly(methacrylate) (PMMA). Each of the above organic polymers, and the monomer units that polymerize to form these polymers, are well known in the art and may be employed.

The organic materials employed are combined in different ratios so as to provide a plurality of sensors, each of which contains a different mole fraction of at least one of the organic materials employed in the fabrication. For example, a plurality of different sensors may be prepared by adding one part of a first polymer to 99 parts of a second polymer to provide the first sensor, adding two parts of a first polymer to 98 parts of a second polymer to provide the second sensor, etc. Therefore, each sensor in the plurality of sensors may be compositionally different.

The sensors are capable of providing a detectable signal in the presence of a chemical analyte of interest. It is a preferred characteristic of the sensors that the detectable signal, or response, is not linearly related to the mole fraction of at least one of the organic materials present in the sensor elements. Further, the response is not a sum or average of the individual responses of each of the components of the sensor. Such non-linearity in response is preferable because arrays of compositionally different sensor elements will optimally provide additional information and resolution of detection if non-linearity of response exists. In other words, if the magnitude of the detectable signal is linearly related to the mole fraction of the components present in the sensor elements, not much additional information can be obtained from sensors comprising a mixture of two different components as compared to that which can be obtained by using only two sensors, each of which being fabricated from only a single polymer component. Thus, the detectable signal produced by the sensor is not linearly related to the mole fraction of at least one of the organic materials used during sensor fabrication.

The step of combining the polymers or monomer units can be performed by a variety of different techniques such as, but not limited to, solution casting, suspension casting, and mechanical mixing. In general, solution cast routes are advantageous because they provide homogeneous structures and ease of processing. With solution cast routes, sensors may be easily fabricated by spin, spray or dip coating. Suspension casting still provides the possibility of spin, spray or dip coating but more heterogeneous structures than with solution casting are expected. With mechanical mixing, there are no solubility restrictions since it involves only the physical mixing of the sensor element components, but device fabrication is more difficult since spin, spray and dip coating are no longer possible. A more detailed discussion of each of these follows.

For systems where the components of the sensors are soluble in a common solvent, the sensors can be fabricated by solution casting. In embodiments where sensors, for example, polymers, are soluble in a common solvent, the use of such miscible solutions has an added advantage. In a series of test tasks, the resolving power of a sensor array containing miscible blends was shown to be superior to that of arrays containing an identical number of sensors that are comprised of only the two base polymeric materials.

In suspension casting, one or more of the components of the sensor is suspended and the others dissolved in a common solvent. Suspension casting is a rather general technique applicable to a wide range of species, which can be suspended in solvents by vigorous mixing or sonication. Mechanical mixing is suitable for all of the possible component permutations. In this technique, the components are physically mixed in a ball-mill or other mixing device.

In one embodiment, the combining step is performed by spraying a first polymer or monomer in a left to right direction across a grid which comprises multiple wells, wherein the concentration of the first polymer or monomer is smoothly varied as the spray travels across the grid. Once the first polymer or monomer is applied to the surface of the grid, a second polymer or monomer is sprayed from a top to bottom direction across the surface of the grid, wherein the concentration of the second polymer or monomer is smoothly varied as the spray travels across the surface of the grid. This process provides a plurality of polymer- or polymer blend-based sensor elements, each of which comprises a different mole fraction of the first and/or second polymer or monomer employed in the fabrication.

An embodiment of a method for manufacturing an array of chemically sensitive sensors from a limited number of feedstock solutions of nonconductive organic materials can be carried out by the following method. First, the following are provided: a first feedstock solution of a first organic material at a concentration x in a first solvent, a second feedstock solution of a second organic material in a second solvent at three different concentrations, y, y+b and y+c, and a substrate having first, second and third preselected regions.

In some embodiments, these preselected regions are physically separated on the substrate. In certain embodiments, the regions are recessed below the surface of the substrate forming wells. In other embodiments, ridges surround the regions on the surface of the substrate. In some of these embodiments, the ridges are formed from photodefinable material. In other embodiments, the ridges are formed from sputtered material.

Next, each of the first, second and third regions is contacted with the first feedstock solution at concentration x. Then, the first region is contacted with the second feedstock solution at concentration y, the second region is contacted with the second feedstock solution at said concentration y+b, and the third region is contacted with the second feedstock solution at said concentration y+c. In this embodiment, the first organic material is different from the second organic material and y, y+b and y+c are each different concentrations. The resulting sensor array has a total number of sensors, one manufactured at each preselected region, that is greater than the number of feedstock solutions used to manufacture the sensors.

In a preferred embodiment, the method of contacting is spraying. In other embodiments, the method of contacting includes pipetting, micropipetting, depositing, spinning, evaporating, dipping, flowing and the like. In some embodiments, the method further includes the step of varying the concentration of the second organic material in the second solution from y to y+b or from y+b to y+c. In certain of these embodiments, the concentration is smoothly varied. In yet other embodiments, after the step of varying the concentration, the method further includes the step of moving the solution from the first region to the second region. For instance, in certain embodiments using spraying as the contacting method, a spraying unit contacts the first, second and third regions and delivers the first solution at concentration x. Then a spraying unit contacts the first region and delivers the second solution at concentration y. Then the concentration is smoothly varied to concentration y+b as the second solution is moved to the second region and contacts the second region delivering the solution at concentration y+b. Finally, the concentration is smoothly varied to concentration y+c as the second solution is moved to the third region and contacts the third region delivering the solution at y+c. In certain embodiments where the sensors to be produced are chemically sensitive resistors, the first feedstock solution further comprises a conductive material, or a third feedstock contains said conductive material, which can also be varied in concentration.

In certain embodiments, these preselected regions are arranged in an array or grid. In some embodiments, the concentrations of both nonconductive organic materials are varied. As a simple example, an embodiment is formed where 4 sensors are arranged in a square grid with the first sensor in the upper left corner, the second sensor in the upper right corner, the third sensor in the bottom left corner and the fourth sensor in the bottom right corner. The previously described spraying unit or units can be used as described above to form the sensors. The first solution is sprayed from top to bottom with the concentration smoothly varied from x to x+a. Then the second solution is sprayed from left to right with the concentration smoothly varied from y to y+b. The resulting combinatorial sensor array contains four sensors, each with a different mole fraction of first and second organic materials. In some embodiments, the direction of spraying is altered. In other embodiments, sensor arrays contain more than 4 sensors. Some embodiments can contain $10^6$ sensors. In certain embodiments, sensor arrays are arranged in shapes other than squares. For instance, arrays may be arranged in shapes such as rectangles, circles, ovals, triangles, rhomboids, diamonds and the like. In some embodiments, arrays are arranged in shapes that produce the most sensors when the array is fabricated on a silicon wafer.

In certain embodiments, the organic materials can be polymers. Where the organic materials are polymers, in certain embodiments, the first polymer is different from the second polymer. In other embodiments, the organic materials are monomers, and the method further includes the step of polymerizing the monomers by applying an activating agent. These activating agents include light, heat and chemicals. In some embodiments, the first solution is miscible in the second solution. In certain of these embodiments, the first solvent is the same as the second solvent.

The sensors that are prepared by these methods are capable of providing a detectable signal in response to contact with a chemical analyte. Specifically, the polymer-based sensors are capable of absorbing a chemical analyte which, in some embodiments, causes the polymer to swell, thereby providing a signal which is capable of detection. Numerous apparati are known in the art and/or may be configured to detect the swelling of the sensor.

In a preferred embodiment, an electrically conductive material is added to the polymer or polymer blend used to fabricate the sensors. In other embodiments, two or more electrically conductive materials are added to the organic material. In these cases, the sensors formed are chemically sensitive resistors.

FIGS. 3 and 4 demonstrate the important concept of using a limited number of feedstock solutions to create a greater number of array sensors. Referring now to FIG. 3, this shows a limited number (n) of polymer feedstock solutions that have been combined to produce a greater number of combinatorial sensors. The feedstock solutions along the top of the matrix ($P_1 \ldots P_n$) are at concentration [x]. The same feedstock polymers are shown along the left side of the matrix ($P_1 \ldots P_n$) at concentration [y]. Individual cells in the matrix show the effect of combining the feedstock solutions to produce a sensor. For instance, the cell at column 2, row 1 contains sensor $P_{2[x]}P_{1[y]}$, indicates that this sensor is formed from polymer feedstock $P_2$ at concentration [x] and polymer feedstock $P_1$ at concentration [y]. Of course, the cells along the diagonal contain only one polymer type and, accordingly, are not combinatorial sensors. Thus, it can be seen that a limited number of polymer feedstock solutions can be combinatorially combined to produce a greater number of sensors. For instance, if the matrix is limited to a 4×4 array of feedstock solutions $P_1$ through $P_4$, such an array of 4 polymer feedstocks would produce 12 combinatorial sensors, assuming that x and y are different concentrations. Further, if the array is confined to those sensors in the cells above the diagonal in the 4×4 array, it can be seen that the four feedstocks still produce a greater number of sensors, namely 6. Thus, even if we eliminate sensors that differ from another sensor only in the concentration of the feedstock polymers used, the resulting number of sensors is still greater than the number of feedstock solutions.

Referring now to FIG. 4, the effect of increasing the variety polymer feedstock solutions is shown. The feedstock solutions along the top of the matrix, $P_1 \ldots P_n$ at concentration [x], are the same as in FIG. 3 above. However, here in FIG. 4, the feedstock polymers shown along the left side of the matrix, $P_{n+} \ldots P_{n+m}$ at concentration [y], are different from the feedstock polymers shown along the top of the matrix. As a result, the sensors in the cells along the diagonal now contain combinatorial sensors, in contrast to the diagonal cells of FIG. 3. For instance, the cell at column 2, row 2 contains sensor $P_{2[x]}P_{n+2[y]}$, indicating that this sensor is formed from polymer feedstock $P_2$ at concentration [x] and polymer feedstock $P_{n+2}$, which is different from $P_2$, at concentration [y]. Thus, if this matrix is limited to a 4×4 array of feedstock solutions $P_1$ through $P_4$, along the top, and $P_{n+1} \ldots P_{n+4}$ along the left, such an array of 8 polymer feedstocks would produce 16 combinatorial sensors, regardless of whether x and y are different or the same concentrations.

The limited feedstock concept is demonstrated in an embodiment of an electronic nose that mimics a mammalian olfactory system, that includes a substrate having a plurality of array sensors, where each array sensor includes a chemically sensitive resistor that includes a combination of a first nonconductive organic material at a concentration, a second nonconductive organic material at a concentration, and a conductive material. The first nonconductive organic material is different from the second nonconductive organic material and the number of array sensors is greater than the number of different nonconductive organic materials that form the array sensors. The electronic nose also includes an electrical measuring apparatus electrically connected to the array sensors. In certain embodiments, the first array sensor differs from the second array sensor in the concentration of the first nonconductive organic material.

Another embodiment includes two chemically sensitive resistors and an electrical measuring apparatus electrically connected to the resistors. Each chemically sensitive resistor includes a combination of a first nonconductive organic material at a concentration, a second nonconductive organic material at a concentration, and a conductive material, with the proviso that the first nonconductive organic material is different from the second nonconductive organic material and that the concentration of the first nonconductive organic material of the first resistor is different from the concentration of the first nonconductive organic material of the second resistor. In certain of these embodiments, the first nonconductive organic material of the first resistor is different from the first nonconductive organic material of the second resistor. In other embodiments, the second nonconductive organic material of the first resistor is different from the second nonconductive organic material of the second resistor.

Yet another embodiment includes two chemically sensitive resistors and an electrical measuring apparatus electrically connected to the resistors. As described previously, each chemically sensitive resistor includes a combination of a first nonconductive organic material at a concentration, a second nonconductive organic material at a concentration, and a conductive material, with the proviso that the first nonconductive organic material is different from the second nonconductive organic material. However, in this embodiment, the first nonconductive organic material of the first resistor is the same as the first nonconductive organic material of the second resistor, and the concentration of the first nonconductive organic material of the first resistor is the same as the concentration of the first nonconductive organic material of the second resistor. In certain embodiments, the concentration of the second nonconductive organic material of the first resistor is different from the concentration of the second nonconductive organic material of the second resistor. In other embodiments, the second nonconductive organic material of the first resistor is different from the second nonconductive organic material of the second resistor.

Yet another embodiment is a single sensor for detecting an analyte in a fluid, which includes a chemically sensitive resistor having a resistance, where the resistor includes a combination of a first nonconductive organic material having a resistance, a second nonconductive organic material having a resistance, and a conductive material. The resistance is initially a baseline resistance, when the sensor is free of the analyte. When the sensor is exposed to the analyte, the resistance is a resistance response. An electrical measuring apparatus is electrically connected to the resistor. The resistance of this resistor is nonlinear. In other words, the resistance is different from a sum of the resistance of the first nonconductive organic material and the resistance of the second nonconductive organic material, and further is different from an average of the resistance of the first nonconductive organic material and the resistance of the second nonconductive organic material.

In certain embodiments, the first and second nonconductive organic materials are nonconductive organic polymers and the combination is an organic nonconductive polymer blend. Lists of these organic polymers have previously been cited herein. In one embodiment, the first nonconductive polymer is polyvinyl acetate and the second nonconductive polymer is polymethyl methacrylate. In other embodiments, the nonconductive organic materials are each nonconductive organic monomers, and the combination polymerizes the monomers into an organic polymer. In certain embodiments, the first nonconductive organic monomer is different from the second nonconductive organic monomer. In other embodiments, they are the same.

One or more of a variety of electrically conductive materials may be employed. In some embodiments, the conductive material is an organic conducting polymer. Examples of such organic conducting polymers include poly(anilines), poly(thiophenes), poly(pyrroles), poly (acetylenes), and the like. In other embodiments, the conductive material is a carbonaceous material such as carbon blacks, graphite, coke, $C_{60}$, and the like. In still other embodiments, the conductive material is a charge transfer complex such as tetramethylparaphenylenediaminechloranile, alkali metal tetracyanoquinodimethane complexes, tetrathiofulvalene halide complexes, and the like. In other embodiments, the conductive material is an inorganic conductor such as a metal or a metal alloy. Examples include Ag, Au, Cu, Pt, AuCu alloy, and the like. In other embodiments, the conductive material is a highly doped semiconductor. Examples include Si, GaAs, InP, $MoS_2$, $TiO_2$, and the like. In still other embodiments, the conductive material is a conductive metal oxide. Examples include $In_2O_3$, $SnO_2$, $Na_xPt_3O_4$, and the like. In other embodiments, the conductive material is a superconductor. Examples include $YBa_2Cu_3O_7$, $Tl_2Ba_2Ca_2Cu_3O_{10}$, and the like. In still other embodiments, the conductive material is a mixed inorganic/organic conductor. Examples include tetracyanoplatinate complexes, iridium halocarbonyl complexes, stacked macrocyclic complexes, and the like.

Certain embodiments include a second chemically sensitive resistor that has a resistance. The second resistor includes a combination of a first nonconductive organic material that has a resistance, a second nonconductive organic material that has a resistance, and a conductive material. The resistance of the second chemically sensitive resistor is nonlinear, using the definition provided herein.

In certain embodiments having at least two resistors, the first nonconductive organic material in the first resistor is the same as the first nonconductive organic material in the second resistor, and in certain of these embodiments, the mole fraction of the first nonconductive organic material in the first chemically sensitive resistor is different from the mole fraction of the first nonconductive organic material in the second chemically sensitive resistor. In certain of the embodiments just described, the ratio of the resistance of the first resistor to the resistance of the second resistor is a function of a property different from the ratio of the mole fraction of the first nonconductive organic material in the first resistor to the mole fraction of the first nonconductive organic material in the second resistor, which is yet another example of the nonlinearity of these embodiments. In other embodiments, the second nonconductive organic material in the first resistor is the same as the second nonconductive organic material in the second resistor.

In embodiments with one or more conductive materials, where the sensors swell in response to contact with a chemical analyte, the particles of conductive material in the sensors move farther apart, thereby increasing the resistance to electrical current passing through the sensor. As such, in embodiments where a conductive material is added to the sensors, the sensors will provide (i) an electrical path, (ii) a first electrical resistance in the electrical path in the absence of the analyte, and (iii) a second electrical resistance in the presence of the chemical analyte. Where the sensor is incapable of sorbing the chemical analyte, the first and second electrical resistances will generally be the same. However, where the sensor sorbs the chemical analyte, the second electrical resistance will generally be different than the first electrical resistance. Thus, in embodiments where the sensors include conductive materials, the detectable signal that detects the presence of a chemical analyte in the fluid is a direct current electrical resistance, but could be resistance over time or frequency.

The sensors that are chemically sensitive resistors can be used in a variety of ways. One embodiment is a method for detecting the presence of an analyte in a fluid, which includes the steps of providing an array of sensors that includes two chemically sensitive resistors, each having a resistance response to the fluid and a resistance response to the analyte, and an electrical measuring apparatus electrically connected to the resistors. Each chemically sensitive resistor includes a combination of a first nonconductive organic material at a concentration, a second nonconductive organic material, and a conductive material, with the proviso that the first nonconductive organic material in each resistor is different from the second nonconductive organic material in each resistor and with a further proviso that the concentration of the first nonconductive organic material in the first resistor is different from the concentration of the first nonconductive organic material in the second resistor. The resistors are then exposed to the fluid and resistance responses that occur when the resistors are permeated by the fluid are measured. Then, the measured resistance response of the first resistor is compared to the measured resistance response of the second resistor to determine the presence of the analyte in the fluid.

As indicated previously herein, certain embodiments of this method include nonconductive organic materials that are nonconductive organic polymers. Other embodiments include nonconductive organic materials that are monomers. In some embodiments, the first organic monomer or polymer is different from the second organic monomer or polymer. In embodiments including monomers, the monomers are polymerized to form an organic polymer. Polymerization is induced by exposure of the monomers to an activating agent, such as light, heat or catalytic chemical. In certain embodiments containing more than one resistor, the first organic material in the first resistor is the same as the first organic material in the second resistor and the second organic material in the first resistor is the same as the second organic material in the second resistor. In certain of these embodiments, the concentration of the first organic material in the first resistor is different from the concentration of the first organic material in the second resistor. Thus, a concentration gradient of the first organic material is formed across the resistors in the combinatorial resistor array. Similarly, a concentration gradient of the second organic material is formed across the resistors, as well.

Certain embodiments containing at least two resistors further include the step of providing a known sample of the analyte in solution and exposing the first and second chemically sensitive resistors to the known solution to create a known response pattern to the presence of the analyte. Then, when the sensors are exposed to an unknown fluid, the first measured response and the second measured response are used to create a measured response pattern. This measured response pattern can then be compared to the known response pattern to determine the presence of the analyte in the fluid, the absence of a substance different from the analyte in the fluid or the concentration of the analyte in the fluid.

In other embodiments, an information storage device is coupled to the electrical measuring apparatus, and the method includes the additional step of storing information in the storage device. This information storage device can be coupled to embodiments having one or more sensors. In some embodiments, this information storage device is a computer. In certain embodiments the stored information is the resistance response to the analyte for each resistor. In other embodiments, the stored information is the resistance response of the resistor as a function of time.

In embodiments that have at least two sensors, the stored information can be the known response pattern to the analyte. The method then includes the additional step of comparing the measured response pattern to the known response pattern to determine the presence of the analyte in the fluid, the absence of a substance different from the analyte in the fluid or the concentration of the analyte in the fluid.

In some embodiments, the electrical measuring apparatus includes an integrated circuit. In certain embodiments, the integrated circuit includes neural network-based hardware. In other embodiments, the integrated circuit includes a digital-analog converter.

The methods of fabrication of the sensors described herein allow quick, easy and inexpensive preparation of large numbers of chemically sensitive sensors in a combinatorial fashion. In one embodiment, arrays of compositionally distinct sensors are incorporated into a device that is designed to detect the presence of an analyte in a fluid by providing a detectable response. Such devices include, without limitation, surface acoustic wave sensors, quartz crystal microbalance sensors, polymer-coated fiber optic sensors, devices designed as analogs of the mammalian olfactory system, and the like. In such systems, the array of sensors employed often comprises at least ten, usually at least 100, and often at least 1000 different sensors, though with mass deposition fabrication techniques described herein or otherwise known in the art, arrays of on the order of at least $10^6$ sensors are readily produced. In certain embodiments, arrays of sensor are placed in communication with an apparatus designed to detect and/or measure the signal produced by the sensor array both in the presence and in the absence of the chemical analyte of interest.

As discussed previously, the sensors described herein can be combined with a wide variety of supporting technology to measure sensor response other than resistance. These embodiments include techniques that detect variations in electromagnetic energy, optical properties, capacitance, inductance or impedance and other physical, chemical and electrical properties that may vary in accordance with the response of the sensors. Thus, the applications to which the sensors may be put is very broad.

One embodiment is a sensor that includes two chemically sensitive elements. The first chemically sensitive element, which includes a combination of first and second organic materials, is adapted to provide a detectable response. The organic materials can be any of the suitable materials previously described herein. The detectable response of this first element is nonlinear by the definition provided herein. The second chemically sensitive element, which also includes a combination of first and second organic materials, is also adapted to provide a detectable response. The detectable response of the second element is also nonlinear by the definition provided herein. A detector is operatively associated with the first and second chemically sensitive elements. During use, each of the first and said second chemically sensitive elements gives a detectable response when in contact with the analyte, which is different from the detectable response when the first and second elements are free of the analyte. In some embodiments, the detectable response is a variation in optical transmission and the detector is a spectrophotometer. In other embodiments, the detectable response is a variation in electromagnetic energy, and the detector measures electromagnetic energy.

Other embodiments include methods by which the above-described sensors can be used. One embodiment is a method for detecting the presence of an analyte in a fluid, which first includes the step of providing a first chemically sensitive element as described in the immediately preceding paragraph, where the element has a detectable response to the fluid and a detectable response to the analyte. A second chemically sensitive element is also provided which has a detectable response to the fluid and a detectable response to the analyte. A detector is operatively associated with the first and second chemically sensitive elements. Next, the first and second chemically sensitive elements are exposed to the fluid. Then the detectable response of the first element is measured. As previously described, in one embodiment, this detectable response is optical transmission. In another embodiment, the detectable response is electromagnetic energy. This detectable response of the first element is nonlinear according to the definition provided herein. Next, the detectable response of the second element is measured. This detectable of the second element is also nonlinear, in that it is different from a sum of the detectable response to permeation by the fluid of the first organic material and the detectable response to permeation by the fluid of the second organic material, is different from an average of the detectable response to permeation by the fluid of the first organic material and the detectable response to permeation by the fluid of the second organic material. Next, the measured response of the first element is compared to the detectable response by the analyte for the first element and the measured response of the second element is compared to the detectable response to the analyte for the second element to determine the presence of the analyte in the fluid.

A wide variety of chemical analytes and fluids may be analyzed by the disclosed sensors and arrays so long as the subject analyte is capable generating a differential response across a plurality of sensors of the array. Analyte applications include broad ranges of chemical classes such as organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc., biomolecules such as sugars, isoprenes and isoprenoids, fatty acids and derivatives, etc. Accordingly, commercial applications of the sensors and arrays include environmental toxicology and remediation, biomedicine, materials quality control, food and agricultural products monitoring, and the like.

Further details of these devices and methods are illustrated in the following non-limiting examples.

EXAMPLE 1

Two organic polymers, poly(vinyl acetate)(PVA) and poly(methyl methacrylate) (PMMA), were selected to form compositionally varied sensors to determine if those sensors would be capable of providing a detectable signal which is not linearly related to the mole fraction of either of the organic polymers present in the sensor. Five different VA/PMMA blends were investigated as carbon black-containing chemically sensitive resistors. The combinatorial sensor fabrication was achieved by combining the two initial base polymer feedstocks to produce solutions of PVA/PMMA mixtures having PVA mole fractions of 0.000, 0.292, 0.551, 0.773 and 1.000, respectively. Each stock solution contained 25 mL of tetrahydrofuran (THF) and 250 mg total dissolved organic polymer, with nominally identical procedures used to fabricate all sensors. To introduce the electrically conducting carbon black component into the composite, a 10 mL aliquot of each stock solution was then combined with 43 mg of carbon black. Each carbon black-polymer suspension was sonicated for 10 minutes and was then spin-coated, at 1000 rpm, onto a glass slide.

The sensors were allowed to dry for a minimum of 12 hours before use. Prior to sensor deposition, the glass slide was coated with two gold contacts to allow monitoring of the resistance response of the sensors upon exposure to various test vapors.

FIG. 1 displays a typical sensor response. Upon exposure to a test vapor containing 13.9 ppth (parts per thousand) of methanol in air for 540 seconds starting at the time point designated 180 seconds in the graph, the resistance of the composite film increases and the response then decreases after the vapor exposure is terminated. This behavior has been discussed in detail for a series of pure polymeric compositions that have been used as either carbon black or polypyrrole composites to provide arrays of electrically conductive vapor sensors. Lonergan et al., *Chem. Mater.* 8:2298 (1996) and Freund and Lewis, *Proc. Natl. Acad. Sci. USA* 92:2652 (1995). Specifically, the increase in electrical resistance observed in response to contact with the chemical analyte is a result of the polymeric material of the sensor sorbing the analyte, thereby swelling and increasing the distance between at least some of the carbon black particles present in the sensor and, in turn, increasing the relative electrical resistance.

To assess the performance of the miscible blend sensors, all of the sensors were exposed five times each to five different analytes, with the vapor concentrations arbitrarily chosen to be 13.9 parts per thousand (ppth) of methanol, 5.2 ppth of ethanol, 7.2 ppth of acetone, 2.9 ppth of ethyl acetate and 4.6 ppth of acetonitrile in air at 21° C. Only the maximum differential resistance response relative to the baseline resistance $\Delta R_{max}/R$ was used in the analysis of the array performance carried out in this work. The results are presented in FIG. 2.

Figure 2:
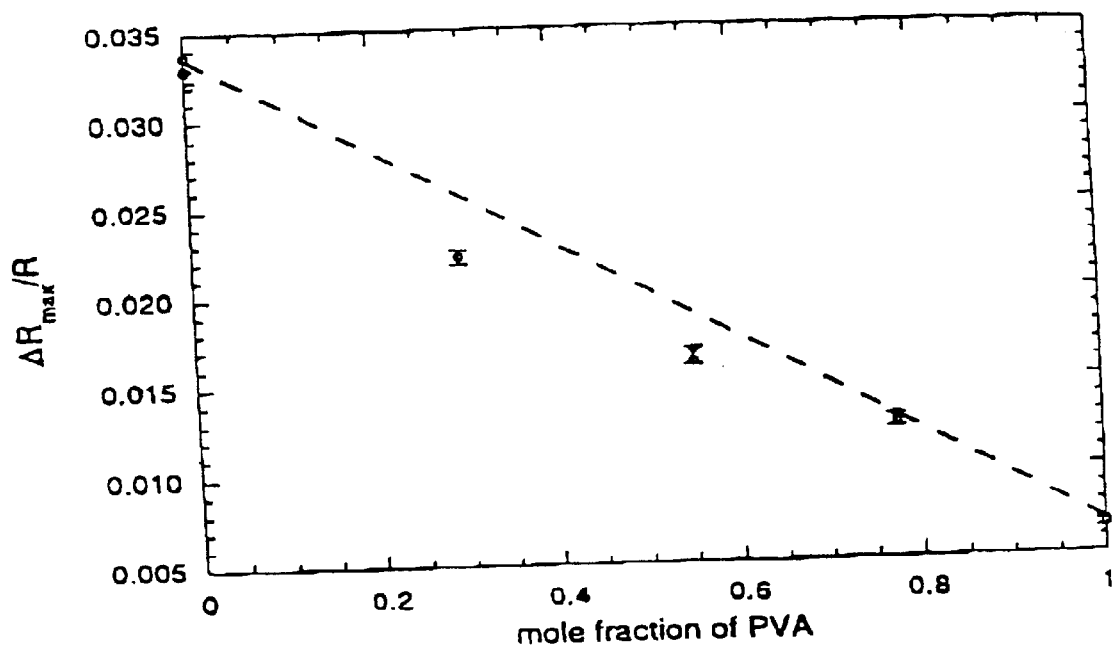
FIG. 2 shows the maximum relative differential resistance response, $\Delta R_{max}/R$, of a series of polymer blend carbon black-containing composite chemically sensitive resistors upon exposure to ethyl acetate. The plot depicts data obtained from 3 sensors of pure PMMA, 2 with 29.2% (by mole fraction) PVA, 2 with 55.1% PVA, 3 with 77.3% PVA and 2 of pure PVA. The responses plotted for each sensor are the mean $\Delta R_{max}/R$ values for 5 exposures to 2.9 ppth ethyl acetate in air. The error bars represent one standard deviation unit of the $\Delta R_{max}/R$ responses averaged over all of the sensors of a given composition. The dashed line is a guide showing the deviation of the data points from linearity.
Figure 5:
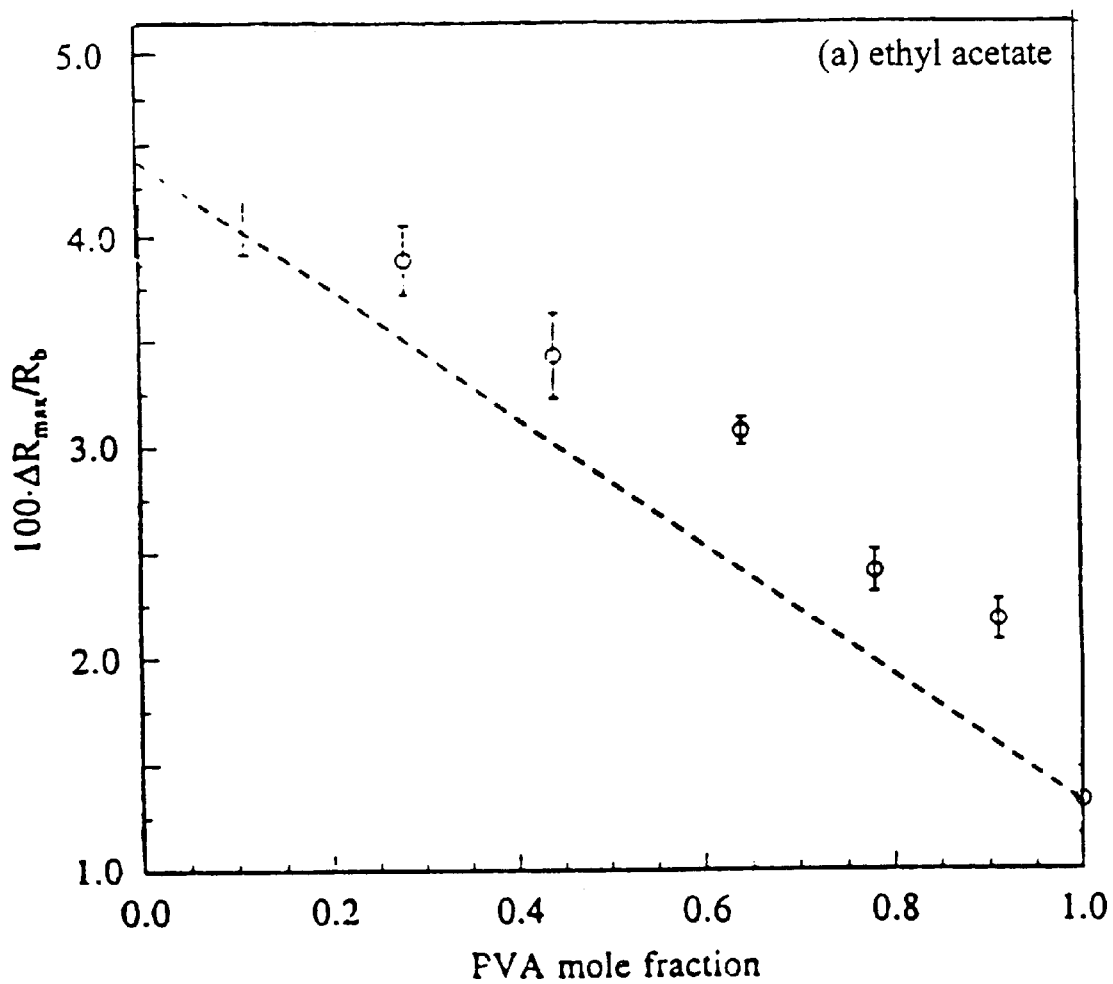
FIG. 5 depicts maximum relative differential resistance response, $\Delta R_{max}/R_b$, of a series of polymer blend-carbon black composite chemiresistors upon exposure to (a) 8.3 ppth of ethyl acetate. The plot of FIG. 5, as well as each of FIGS. 6–9, depict data obtained from 14 detectors of pure PMMA, 10 with 11% (by monomer mole fraction) PVA, 10 with 28% PVA, 15 with 44% PVA, 10 with 64% PVA, 15 with 78% PVA, 10 with 91% PVA, and 15 of pure PVA. The responses plotted for each mole fraction are the mean $\Delta R_{max}/R_b$ values for 10 exposures to each set of detectors containing the specified mole fraction of PVA, while the error bars represent one standard deviation unit. Dashed lines were drawn, joining the end points, as a guide to the eye indicating a linear response relationship.
Figure 6:
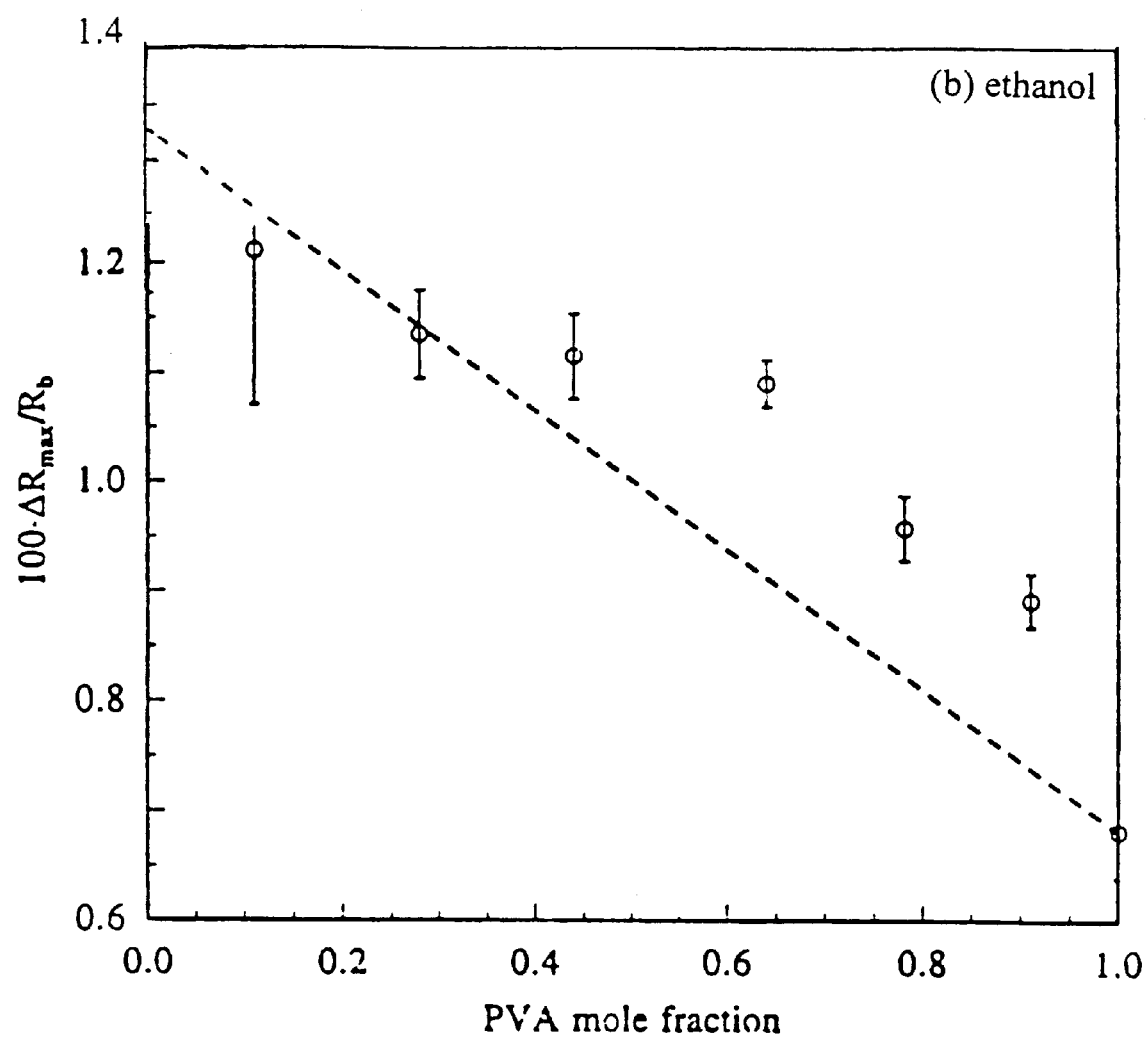
FIG. 6 depicts maximum relative differential resistance response of a series of polymer blend-carbon black composite chemiresistors upon exposure to 5.2 ppth of ethanol.
Figure 7:
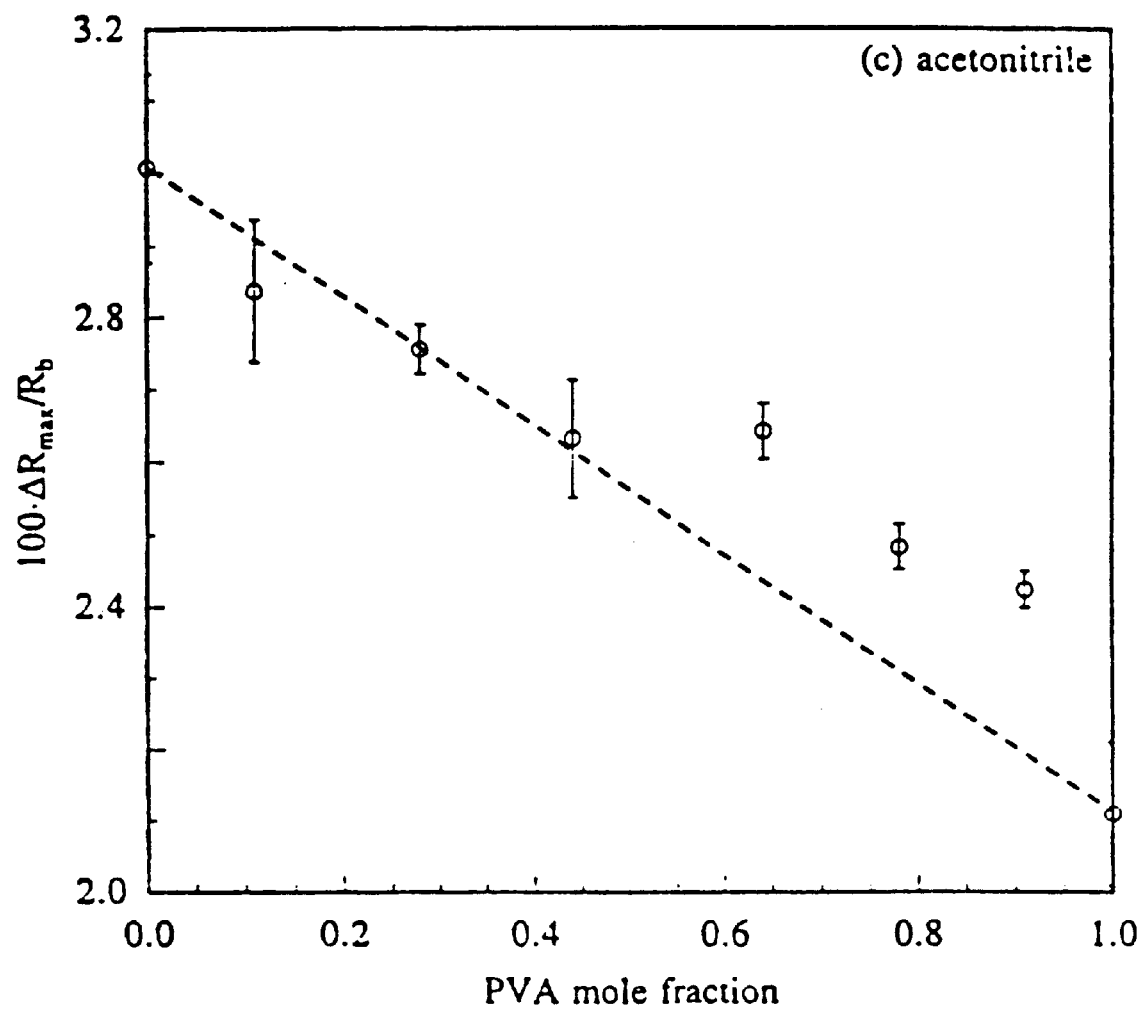
FIG. 7 depicts maximum relative differential resistance response of a series of polymer blend-carbon black composite chemiresistors upon exposure to 8.2 ppth of acetonitrile.
Figure 8:
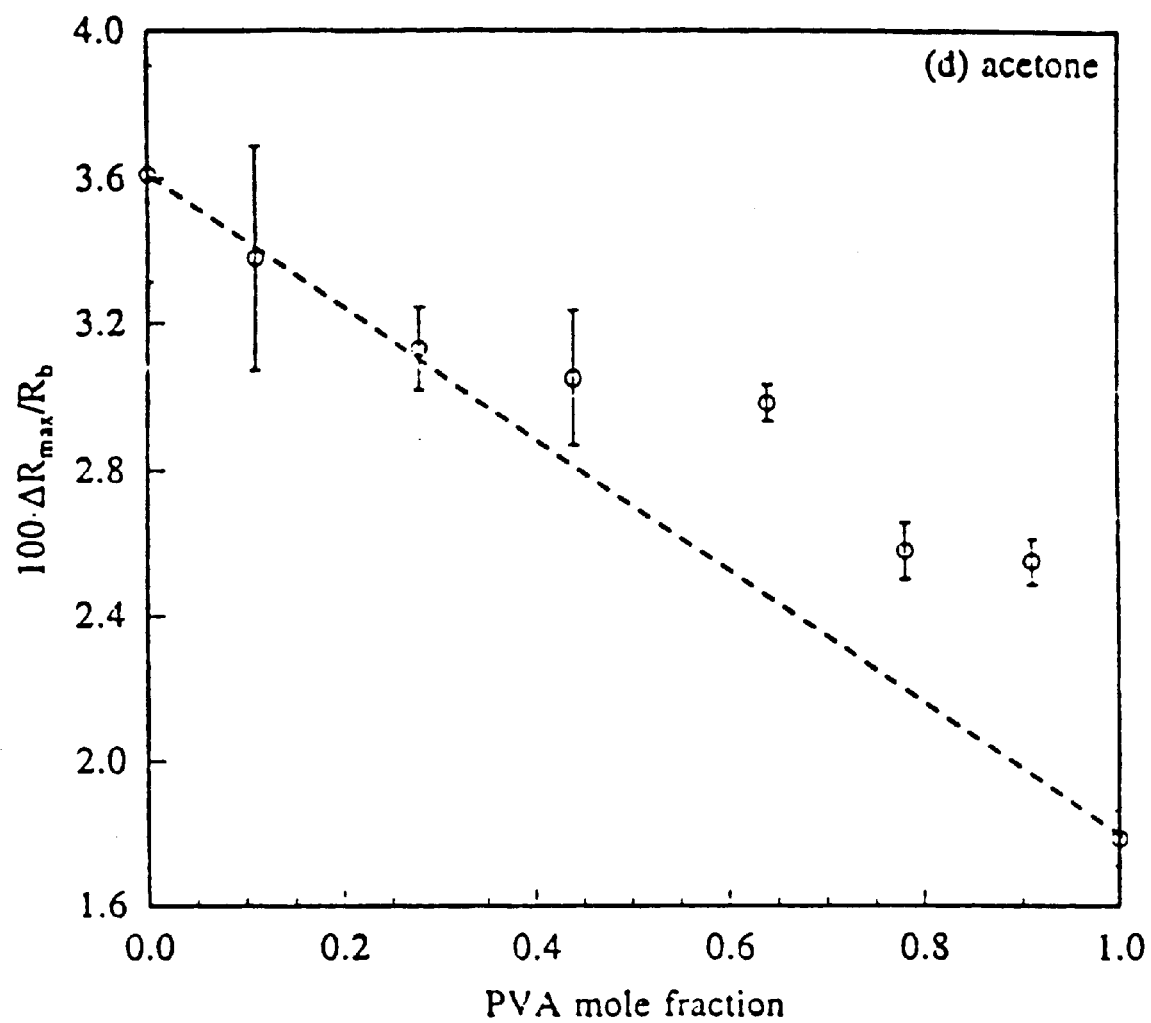
FIG. 8 depicts maximum relative differential resistance response of a series of polymer blend-carbon black composite chemiresistors upon exposure to 20.7 ppth of acetone.
Figure 9:
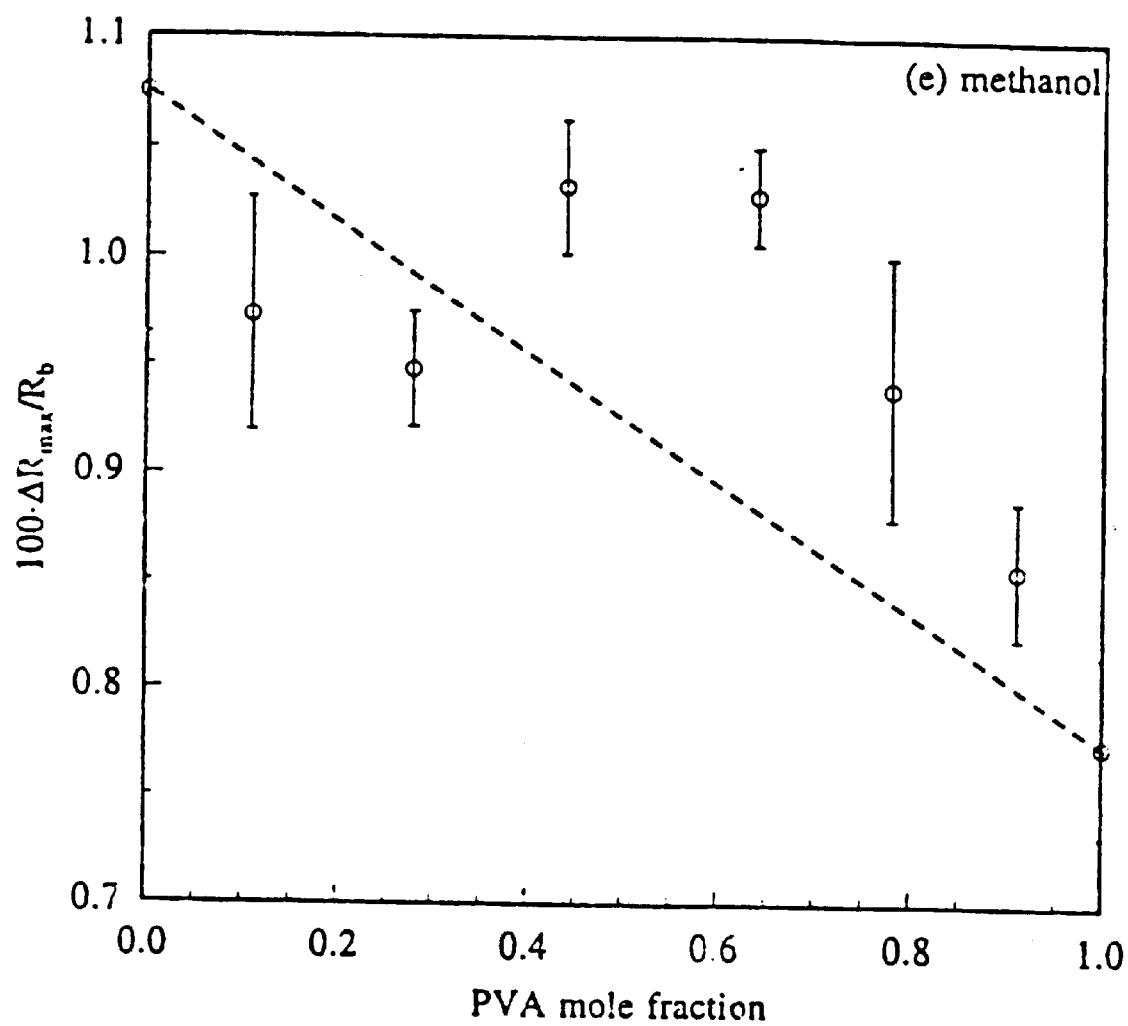
FIG. 9 depicts maximum relative differential resistance response of a series of polymer blend-carbon black composite chemiresistors upon exposure to 11.3 ppth of methanol in air.

FIG. 2 depicts a plot of $\Delta R_{max}/R$ for the polymer blend chemically sensitive resistors upon exposure to ethyl acetate. Similar behavior was observed when methanol, ethanol, acetonitrile or acetone were used as test vapors (data not shown). In all cases, a statistically significant non-linearity was observed for the sensor response versus the mole fraction of the base polymer feedstocks.

This indicates that useful information is available through use of such miscible blend materials in a sensor array for vapor classification.

The ability of a specific sensor array to resolve pairs of solvent vapors can be quantified statistically through reference to a generalized resolution factor, rf. This quantity is equivalent to that proposed by Muller, *Sens. Actuators* B 4:35 (1991) and recently used by Gardner and Bartlett, *Eurosensors IX*, pp. 169 (1995) and is a multi-dimensional analogue to the separation factors used in gas chromatography. Nonlinearity in the gas-solid partition coefficient is crucial to increasing the diversity of a broadly responsive sensor array that is fabricated through combinatorial methods, because otherwise the response of the blended chemically sensitive resistors can be predicted precisely from the responses of the base polymeric sensor materials. No new analyte classification information is therefore provided by the inclusion of the additional sensors into the sensor array without such nonlinear behavior.

The mean response vector, $$\vec{X}_a$$

of an n-sensor array to analyte a is taken as the n-dimensional vector containing the mean response of each sensor, $$\overline{Q_{aj}}$$

to the ath analyte as components such that, $$\vec{X}_a = (\overline{Q_{a1}}, \overline{Q_{a2}}, \ldots, \overline{Q_{an}})$$

The average separation, $$|\vec{d}|$$

between two analytes, a and b, in the Euclidean sensor response space is then just the magnitude of the difference between $$\vec{X}_a$$

and $$\vec{X}_b$$

The reproducibility of the sensor responses to the analytes is also important in quantifying the resolving power of the array. Thus the standard deviations, $$\sigma_{a,\vec{d}}$$

and $$\sigma_{b,\vec{d}}$$

obtained from all the individual array responses to each of a and b in the direction of the vector d, are used to describe the average separation and ultimately define the resolution factor, $$rf = \frac{|\vec{d}|}{\sqrt{\sigma^2_{a,\vec{d}} + \sigma^2_{b,\vec{d}}}}$$

This metric allows quantification of the ability of the sensor array to resolve pairwise the vapors of concern in the test analyte set. Because the functional form of the response of the various polymer chemically sensitive resistors was very similar, this procedure can be used to provide an objective measure of array performance, as opposed to performing a subjective assessment of the performance of task-specific neural network classifiers on functionally dissimilar responses of various array elements. Zupan and Gasteiger, *Neural Networks for Chemists*, VCH, New York, N.Y., pp. 305 (1993).

The responses produced by a set of 12 sensors, three with only PMMA, two with 29.2% mole fraction PVA in PMMA, two with 55.1% mole fraction PVA in PMMA, three with 77.3% mole fraction PVA in PMMA, and two with only PVA, were investigated using this approach. Two criteria were chosen as a measure of the performance of each array: (1) the mean resolution factor of the sensor array for all of the analyte pairs in the test set, and (2) the value of rf produced by that library for the worst-resolved pair of analytes in the test set. The performance of every combination of 5 of the 12 sensors was evaluated to determine if the best-performing set, by either performance criterion, would contain the 5 sensors comprised of only the base polymers or whether some of the combinatorially fabricated polymer blends would be included in the best-performing sensor library. The results of these experiments are presented in Tables 1 to 3.

TABLE 1

Sensor set, including combinatorial sensors, with largest average rf[a]
(avg. rf = 20, worst rf = 2.8)

|  | ethanol | acetonitrile | acetone | ethyl acetate |
|---|---|---|---|---|
| methonol | 15 | 2.8 | 16 | 25 |
| ethanol |  | 25 | 10 | 19 |
| acetonitrile |  |  | 32 | 40 |
| acetone |  |  |  | 15 |

[a]This set of five sensors contained one with only PMMA.

TABLE 2

Sensor set, including combinatorial sensors, with largest average rf[b]
(avg. rf = 19, worst rf = 3.0)

|  | ethanol | acetonitrile | acetone | ethyl acetate |
|---|---|---|---|---|
| methonol | 13 | 3.0 | 28 | 21 |
| ethanol |  | 24 | 9.4 | 15 |
| acetonitrile |  |  | 30 | 33 |
| acetone |  |  |  | 20 |

[b]This set of five sensors contained two with only PMMA, one with 77.3 PVA in PMMA and two with only PVA.

TABLE 3

Sensor set with only single polymer sensors[c]
(avg. rf = 14, worst rf = 3.0)

|  | ethanol | acetonitrile | acetone | ethyl acetate |
|---|---|---|---|---|
| methonol | 12 | 3.0 | 19 | 18 |
| ethanol |  | 14 | 8.1 | 9.1 |
| acetonitrile |  |  | 25 | 20 |
| acetone |  |  |  | 14 |

[c]This set of five sensors contained three with only PMMA and 2 with only PVA.

As clearly shown in Tables 1–3, the inclusion of the combinatorially-fabricated sensors produced a statistically significant improvement in average rf. Large improvements in the resolution of individual vapor pairs, such as acetonitrile from ethyl acetate, or ethanol from ethyl acetate, were obtained by including the combinatorially-fabricated sensors into the sensor library. However, the performance of the array in separating the worst resolved pair of solvents, methanol and acetonitrile, did not improve significantly by including the combinatorially-formed sensors into the library, indicating that further diversity in the base components of the array is required in order to optimize the performance of the array for this particular sensing task.

Another significant conclusion arising from the data presented in Tables 1–3 is that the classification of these various vapors, at fixed concentrations, is statistically robust from the array response even though the individual sensors themselves were not designed to possess high selectivity toward a specific analyte. For example, a pairwise resolution factor of 8 implies that, in a single presentation of the challenge vapors to the sensor array, a given vapor can be distinguished from the other member of the test pair statistically with >99.999% confidence level. This level of performance was met or exceeded by the best-performing five element polymer blend sensor arrays for essentially all of the test vapor pairs used in this work (except methanol-acetonitrile, which were only distinguished at approximately a 96% confidence in a single presentation), even though the array elements were not chosen in advance specifically to perform any particular set of vapor classification tasks.

Exploitation of a nonlinear response of binary, tertiary, and quaternary blend chemically sensitive resistors to various solvent vapors should offer the opportunity to increase significantly the diversity of a polymer composite sensor library and, therefore, to increase its classification performance relative to a library that contains chemically sensitive resistors fabricated from the pure polymeric phases alone.

The olfactory bulb of canines has approximately 100 million receptor cells and that humans have over 1000 different olfactory receptor proteins. Axel, Sc. Am. 154 (1995). Thus, attempts to mimic functionally the olfactory sense are more likely to be realizable with exploitation of combinatorial sensor library methodologies to incorporate extensive diversity into a polymer-based vapor sensing array. Certain embodiments provide novel methods for preparing highly diverse libraries of chemically sensitive sensors.

EXAMPLE 2

Compatible blends of poly(vinyl acetate) and poly(methyl methacrylate) have been used to produce a series of electrically conducting carbon black composites whose resistance is sensitive to the nature and concentration of an analyte in the vapor phase. See Lewis, Grubbs, Severin, Sanner and Doleman, "Use of Compatible Polymer Blends to Fabricate Arrays of Carbon Black-Polymer Composite Vapor Detectors," *Analytical Chemistry*, in press (1998), incorporated herein by reference in its entirety. The dc electrical resistance response of the composites was found to be a nonlinear function of the mole fraction of poly(vinyl acetate) in the blend. These compatible blend composite detectors provided additional analyte discrimination information relative to a reference detector array that only contained composites formed using the pure polymer phases. The added discrimination power provided by the compatible blend detectors, and thus the added diversity of the enhanced detector array, was quantified through use of a statistical metric to assess the performance of detector arrays in various vapor classification tasks.

Eight different PVA/PMMA blend compositions were investigated as carbon black composite chemiresistor vapor detectors. The compatible blend detector fabrication was achieved by combining the two initial base polymer feedstocks to produce solutions of PVA/PMMA having PVA mole fractions (by monomer) of 0.00, 0.11, 0.28, 0.44, 0.64, 0.78, 0.91, and 1.00, respectively. Each stock solution contained 20 mL of tetrahydrofuran, 200 mg of total dissolved polymer, and 86 mg of suspended carbon black. Standard glass microscope slides, cut to a size of approximately 2 cm×2.5 cm, were modified for use as the substrate for each polymer blend detector. Two parallel bands of 20 nm thick chromium ($\approx$2 cm×1 cm), spaced apart 0.5 cm, were evaporated onto each slide. The chromium bands were then coated with 30 nm of evaporated gold, thus forming robust electrical contacts. Each carbon black-polymer suspension was sonicated for 10 minutes and was then spin-coated, at 1000 rpm, onto a modified glass slide such that the gap between the slide electrical contacts was spanned by the polymer composite film. The detectors were allowed to dry in ambient air for 12 hours before use.

To obtain response data, the detectors were placed into a 1.2 L sampling chamber and electrical leads were attached to the two chromium-gold bands of each detector. The dc resistance of each detector was recorded as a function of time using a Keithley model 7001 channel switcher connected to a Keithley model 2002 multimeter that was interfaced to a personal computer. An automated flow system consisting of LabVIEW software, a personal computer, and electrically controlled solenoid valves and mass flow controllers was used to produce and delivery controlled concentrations of solvent vapors to the detectors in the sampling chamber. The desired vapor concentrations were obtained by passing a stream of carrier gas through a bubbler that had been filled with the solvent of choice and then diluting this flow into a stream of air maintained at a controlled flow rate. The time protocol for each exposure was 120 s of air, followed by 600 s of test vapor in air, ending with another 600 s of air.

Figure 10:
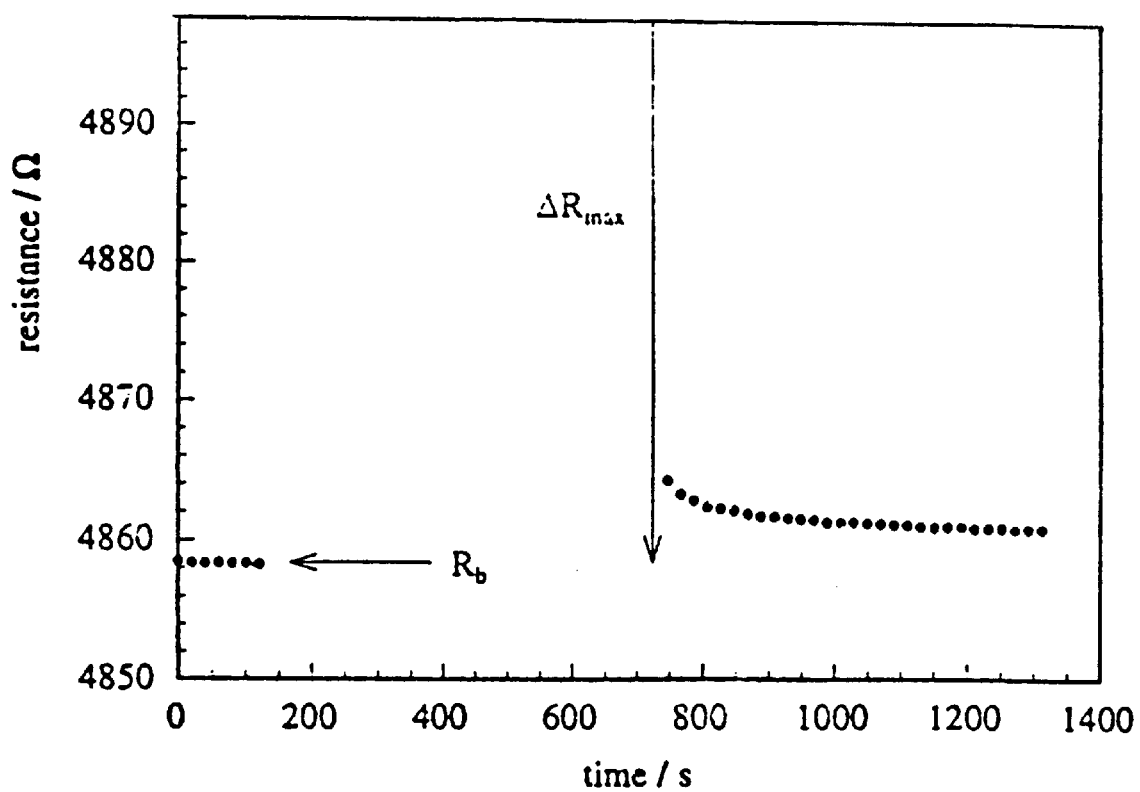
FIG. 10 depicts temporal resistance response of a typical polymer composite chemiresistor detector. This particular carbon black composite detector contained 64% PVA and 36% PMMA by monomer mole fraction. The detector was exposed to 11.3 ppth of methanol in air for 600 s starting at t=120 s. The baseline resistance before the exposure $R_b$, and the maximum resistance change during the exposure, $\Delta R_{max}$, were 4858 and 50 Ω, respectively.

FIG. 10 displays the resistance response of a typical detector. Upon exposure to a test vapor, the resistance of the composite film increased, and the response then decreased after the vapor exposure was terminated. This behavior has been discussed in detail for a series of pure polymeric compositions that have been used as either carbon black or polypyrrole composites to provide different analytes, with the vapor concentrations chosen to be 11.3 parts per thousand (ppth) of methanol, 5.2 ppth of ethanol, 20.7 ppth of acetone, 8.3 ppth of ethyl acetate, and 8.2 ppth of acetonitrile in air at 21° C. these concentrations all correspond to 7.1% of the solvent-saturated concentration of each analyte in 21° C. air, under a total atmospheric pressure of 753 Torr. The maximum differential resistance response relative to the baseline resistance ($\Delta R_{max}/R_b$) was used in the analysis of the array performance carried out in this work.

FIGS. 5–10 depict plots of $\Delta R_{max}/R_b$ for the polymer bland chemiresistors upon exposure to acetate, ethanol, acetonitrile, acetone, and methanol. For each analyte, a statistically significant nonlinearity was observed for the detector response versus the mole fraction of the base polymer feedstocks. Since the nonlinearity is not the same for all solvents, this indicates that useful information is available through use of such compatible blend materials in a detector array for vapor classification.

The ability of a specific detector array to resolve pairs of solvent vapors can be quantified statistically through reference to a generalized resolution factor, rf. This quantity is equivalent to that proposed by Miller et al., [need citation] and recently used by Gardner and Bartlett [need citation] and is multidimensional analogue of the separation factors used in gas chromatography. Resistance responses, $\Delta R_{max}/R_b$, of carbon black-polymer composite detectors, containing $\geq$20 wt. % carbon black, have been shown to vary linearly over at least an order of magnitude in the concentration of the analyte in the vapor phase. Hence, detector arrays which can resolve analytes at one concentration can also be used to resolve analytes at other concentrations. The detector responses were autoscaled to account for the different dynamic ranges of different detectors. The autoscaled response of the jth detector to the ith exposure, $A_{ij}$ was thus $$A_{ij} = \frac{(\Delta R_{ij,\max} / R_b) - \alpha_j}{\beta_j} \quad (1)$$

where $\alpha j$ and $\beta j$ are the mean and standard deviations, respectively, in the responses of the jth detector to all analytes. The mean response vector, $\vec{X}_a$, of an n-detector array to analyte a is taken as the n-dimensional vector containing the mean autoscaled response of each detector $\vec{A}_{aj}$, to the ath analyte such that $$\vec{X}_a = (\vec{A}_{a1}, \vec{A}_{a2}, \ldots, \vec{A}_{an}) \quad (2)$$

The average separation, $|\vec{d}|$, between two analytes, a and b, in the Euclidean detector response space is then simply the magnitude of the difference between $\vec{X}_a$ and $\vec{X}_b$. The reproducibility of the array responses to the analytes is also important in quantifying the resolving power of the array. A measure of array response reproducibility to analyte, a, $\sigma_{a,\vec{a}}$, is obtained by projecting the array response vectors for each exposure to analyte a onto the vector $\vec{d}$, and calculating the standard deviation in these scalar projections about the projection of the mean response vector, $\vec{X}_a$ onto $\vec{d}$. The same procedure is repeated for analyte b of the a,b analyte pair, allowing a pairwise resolution factor to be defined as $$rf = \frac{|\vec{d}|}{\sqrt{\sigma_{a,\vec{d}}^2 + \sigma_{b,\vec{d}}^2}} \quad (3)$$

This metric allows quantification of the ability to resolve pairwise the vapors of concern in the test analyte set based on the response patters that they produce on the detector array. Because the functional form of the response of the various polymer composite chemiresistors was very similar, this procedure can be used to provide an objective measure of array performance, as opposed to performing a subjective assessment of the performance of task-specific neural network classifiers on functionally dissimilar responses of various array elements. It is important to realize, however, that the results are nevertheless coupled to the metric used to evaluate the response and that different algorithms, such as, for example, Fisher linear discriminants, which are linear data analysis methods that are not confined to pass through the mean response values of the analytes of concern, may well yield different conclusions from the same response data.

The response produced by a set of 99 detectors, 14 detectors with pure PMMA, 10 with 11% PVA, 10 with 28% PVA, 15 with 44% PVA, 10 with 64% PVA, 15 with 78% PVA, 10 with 91% PVA, and 15 with pure PVA, were investigated using this approach. The performances of 8-detector combinations from different sets of detectors were evaluated to determine if arrays containing some of the compatible blend polymer detectors would perform better than arrays containing only detectors made from the base polymers, for certain test tasks. The performance of each studies array was measured by its ability to resolve the solvents pairwise, as given by the calculated rf values obtained using the simple linear data analysis method described above.

Results are presented for four sets of detectors. Set A contained all 14 detectors with 0% PVA and all 15 detectors with 100% PVA (i.e., all the base polymer detectors). Set B contained all 99 of the prepared detectors ranging from 0% through to 100% PVA content. Set C contained only the 10 detectors with 91% PVA. Set D contained all 14 of the 0% PVA detectors, all 10 of the 91% PVA detectors, and all 15 of the 100% PVA detectors. Since there are extremely large numbers of possible 8-detector combinations from within sets A, B, and D ($\approx 10$ unique 8-detector combinations out of 99 set B detectors), 500-member subsets of the total number of 8-detector array combinations were selected randomly and their corresponding rf values were calculated. For set C, rf values for all 45 possible 8-detector combinations out of 10 detectors were calculated. The results of the calculated resolution factors for arrays of 8-detectors within each set were averaged and are presented in Table 4, below.

100% PVA content. Set C contained only the 10 detectors with 91% PVA. Set D contained all 14 of the 0% PVA detectors, all 10 of the 91% PVA detectors, and all 15 of the 100% PVA detectors.

Clearly, the inclusion of compatible blend detectors produced a statistically significant improvement in maximizing the overall average rf, which is the average ability of all calculated 8-detector array combinations within a set of detectors to resolve all analyte pairs using the metric defined above. For example, sets B, C, and D, which contained compatible blend detectors, had overall average rf's of 60, 81, and 60, respectively, whereas the base polymer detector arrays (set A) had an overall average rf of 52. The array performance in separating the pair of solvents, ethyl acetate vs. acetone, that was worst resolved by set A (base polymer detectors) could also be improved by using 8-detector arrays containing only 91% PVA detectors (set C) or by including these detectors in arrays that contained the base polymer detectors (set D). Set D arrays, containing blended polymers, exhibit a larger overall average rf, a larger rf for the worst resolved analyte pair, and resolved 7 of the 10 analyte pairs better than did the base polymer arrays of set A.

Another significant conclusion arising from the data is that the classification of these various vapors, at fixed concentrations, is statistically robust from the array response even though the individual detectors themselves were not designed to possess high selectivity toward a specific analyte. For example, a pairwise resolution factor of 4.5 implies that, in a single presentation of the challenge vapors to the detector array, a given vapor can be . . . was met or exceeded by all of the eight-element detector arrays of Table 4 for all of the test vapor pairs used in this work, even though the array elements were not chosen in advance specifically to perform any particular set of vapor classification tasks.

Utilization of a nonlinear response of binary, tertiary, and quaternary blend composite chemiresistors to various solvent vapors should offer the opportunity to increase significantly the diversity of a polymer composite detector array and therefore to increase its classification performance relative to an array that contains chemiresistors fabricated from the pure polymeric phases alone. The binary polymer blend advantages reported herein are in agreement with those recently published using a different detector modality,

TABLE 4

| Sensors used | Overall avg. rf | vs ethanol | vs ethyl-acetate | vs acetonitrile | vs. acetone | vs ethyl acetate | vs acetonitrile | vs acetone | acetate vs acetonitrile | acetate vs acetone | vs acetone |
|---|---|---|---|---|---|---|---|---|---|---|---|
| Set A | 52 | 25 | 61 | 90 | 44 | 58 | 93 | 42 | 58 | 20 | 27 |
| Set B | 60 | 19 | 67 | 104 | 81 | 67 | 110 | 81 | 31 | 17 | 26 |
| Set C | 81 | 4.6 | 122 | 102 | 181 | 103 | 93 | 148 | 17 | 31 | 8.7 |
| Set D | 60 | 23 | 84 | 93 | 60 | 82 | 96 | 58 | 55 | 22 | 26 |

The overall average rf represents the average resolution factor across all analyte pairs for random combinations of detectors from a given detector set. The results for set A, set B, and set D were obtained by averaging over 500 randomly selected 8-detector arrays composed of only the detectors within each respective set. The results for set C were obtained by averaging over all 45 possible 8-detector combinations of the detectors within the set. Set A contained all 14 of the 0% PVA detectors and all 15 of the 100% PVA detectors (i.e., all the base polymer detectors). Set B contained all 99 of the prepared detectors ranging from 0% to polymer-dye optical detectors. The exact performance gain of any specific array will likely be task dependent and must be evaluated for each application of concern. We note, however, that the olfactory bulb of canines has approximately 100 million receptor cells and that humans have over 1000 different . . . into a polymer-based vapor-sensing array. Extension of the approach described herein to other blends and a comparison of the detector diversity that can be achieved through the use of block and random copolymers as a complement to the use of compatible blends in detector arrays will be reported separately.

While particular devices and methods have been described for producing compositionally different polymer-based sensors, once this description is known, it will be apparent to those of ordinary skill in the art that other embodiments and alternate steps are also possible without departing from the spirit and scope of the invention. Moreover, it will be apparent that certain features of each embodiment as well as features disclosed in each reference incorporated herein, can be used in combination with devices illustrated in other embodiments. Accordingly, the above description should be construed as illustrative, and not in a limiting sense, the scope of the invention being defined by the following claims.

What is claimed is:

1. A sensor array for detecting an analyte in a fluid, comprising:
    a substrate having an array of sensors, each sensor comprising a combination of a first organic material at a concentration, and a second organic material at a concentration; and
    a detector operatively associated with each said sensor, wherein the first organic material is different from the second organic material and wherein the number of compositionally different sensors is greater than the number of different organic materials which form the sensors.

2. The sensor array of claim 1, wherein each sensor comprises a chemically sensitive resistor.

3. The sensor array of claim 1, wherein the first organic material is a nonconductive organic material.

4. The sensor array of claim 1, wherein the second organic material is a nonconductive organic material.

5. The sensor array of claim 1, wherein each sensor further comprises a conductive material.

6. The sensor array of claim 1, wherein the detector is an electrical measuring apparatus electrically connected to said sensors.

7. The sensor array of claim 1, wherein the first organic material is a copolymer.

8. The sensor array of claim 1, wherein the first organic material is a homopolymer.

9. The sensor array of claim 1, wherein the first organic material is a block copolymer.

10. The sensor array of claim 1, wherein the first and second organic materials are homopolymers.

11. A sensor array for detecting an analyte in a fluid, comprising:
    a first sensor comprising a combination of a first organic material at a concentration and a second organic material at a concentration, with the proviso that the first organic material is different from the second organic material;
    a second sensor comprising a combination of a first organic material at a concentration and a second organic material at a concentration, with the proviso that the first organic material is different from the second organic material and the concentration of the first organic material of the first sensor is different from the concentration of the first organic material of the second sensor, wherein the number of compositionally different sensors is greater than the number of different organic materials which form the sensors; and
    a detector operatively associated with each said sensor.

12. The sensor array of claim 11, wherein each sensor comprises a chemically sensitive resistor.

13. The sensor array of claim 11, wherein the first organic material is a nonconductive organic material.

14. The sensor array of claim 11, wherein the second organic material is a nonconductive organic material.

15. The sensor array of claim 11, wherein the first and second sensors further comprise a conductive material.

16. The sensor array of claim 11, wherein the detector is an electrical measuring apparatus electrically connected to said sensors.

17. The sensor array of claim 11, wherein the first organic material of the first sensor is a copolymer.

18. The sensor array of claim 11, wherein the first organic material of the first sensor is a homopolymer.

19. The sensor array of claim 11, wherein the first organic material of the first sensor is a block copolymer.

20. The sensor array of claim 11, wherein the first and second organic materials of the first sensor are homopolymers.

21. The sensor array of claim 1, wherein at least one sensor is an interpenetrating network comprising a first polymer and a second polymer formed from a monomer polymerized in the presence of the first polymer.

22. The sensor array of claim 11, wherein the first sensor is an interpenetrating network comprising a first polymer and a second polymer formed from a monomer polymerized in the presence of the first polymer.

23. The sensor array of claim 1, wherein one sensor of the array of sensors is a member selected from the group consisting of a coated surface acoustic wave sensor, a fiber optic micromirror, a quartz crystal microbalance sensor and a polymer-coated fiber optic sensor.

24. The sensor array of claim 1, wherein said detector comprises a neural network.

* * * * *

UNITED STATES PATENT AND TRADEMARK OFFICE
CERTIFICATE OF CORRECTION

PATENT NO.    : 6,290,911 B1
DATED         : September 18, 2001
INVENTOR(S)   : Lewis et al.

It is certified that error appears in the above-identified patent and that said Letters Patent is hereby corrected as shown below:

<u>Column 1,</u>
Line 8, insert the following new paragraph:
-- The U.S. Government has certain rights in this invention pursuant to Grant No. CHE-9202583 awarded by the National Science Foundation. --

Signed and Sealed this

Thirtieth Day of April, 2002

*Attest:*

*Attesting Officer*

JAMES E. ROGAN
*Director of the United States Patent and Trademark Office*